(12) United States Patent
Amendola et al.

(10) Patent No.: US 11,974,935 B2
(45) Date of Patent: *May 7, 2024

(54) UNIVERSAL DYNAMIC ATHLETIC ANKLE BRACE AND ADD-ON INTERIOR STIRRUP SUPPORT SYSTEM

(71) Applicant: RUBBER CITY BRACING COMPANY LLC, Akron, OH (US)

(72) Inventors: Annunziato Amendola, Durham, NC (US); Anthony Perera, Cardiff (GB); Bryan Den Hartog, Urbandale, IA (US); David B. Kay, Akron, OH (US); Nicholas Gomez, San Marcos, CA (US); Ian D. Kovacevich, Carlsbad, CA (US); Nouphone J. Bansasine, Temecula, CA (US)

(73) Assignee: RUBBER CITY BRACING COMPANY LLC, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/993,664

(22) Filed: Nov. 23, 2022

(65) Prior Publication Data

US 2023/0091998 A1     Mar. 23, 2023

Related U.S. Application Data

(63) Continuation of application No. 17/686,388, filed on Mar. 3, 2022, now Pat. No. 11,607,331.

(51) Int. Cl.
*A61F 5/01* (2006.01)
(52) U.S. Cl.
CPC ..... *A61F 5/0111* (2013.01); *A61F 2005/0197* (2013.01)

(58) Field of Classification Search
CPC .... A61F 5/0111; A61F 5/0127; A61F 5/0585; A61F 2005/0197; A43B 3/16;
(Continued)

(56) References Cited

U.S. PATENT DOCUMENTS 3,958,573 A     5/1976   Wiley
5,474,524 A     12/1995  Carey
(Continued)

OTHER PUBLICATIONS

Cohen, Randy, Unraveling the Confusing Web of Neoprene Materials, Nov. 18, 2020 [online], [retrieved on Nov. 1, 2023]. Retrieved from the Internet <URL: https://www.franklowe.com/neoprene-materials/ (Year: 2020).

*Primary Examiner* — Keri J Nelson
(74) *Attorney, Agent, or Firm* — TILLMAN WRIGHT, PLLC; Chad D. Tillman

(57) ABSTRACT

A rear-entry ankle brace includes an elastomeric component defining an inside elbow channel configured to span an ankle joint. A channel opening extends the length of the elastomeric component for direct insertion on top of a leg. One or more leg straps are used to adjustably tension first and second rear edges of the channel opening toward one another and secure the brace to the lower leg. Two foot straps are used to adjustably tension first and second bottom edges of the channel opening toward one another and secure the brace to the mid-foot. The foot straps overlap on the bottom to define a plantar surface of the brace and cross over each other on the topside of the elastomeric component and are secured to a leg strap. A pair of stabilizing stirrups optionally are included on the inside surfaces of the elastomeric component and receive the malleoli.

20 Claims, 13 Drawing Sheets

(58) Field of Classification Search
CPC .. A43B 3/163; A43B 3/18; A43B 3/20; A43B 7/18; A43B 7/20; A41D 17/00; A41D 17/005
See application file for complete search history.

(56) References Cited

U.S. PATENT DOCUMENTS

| | | | |
|---|---|---|---|
| 5,507,720 A | | 4/1996 | Lampropoulos |
| 5,628,733 A | | 5/1997 | Zinreich et al. |
| 5,897,520 A | | 4/1999 | Gerig |
| 5,921,945 A | * | 7/1999 | Gray ................... A61F 5/05866 602/5 |
| 7,127,836 B1 | * | 10/2006 | Jamison ................... A43B 7/32 36/7.2 |
| 7,993,329 B2 | | 8/2011 | Howell et al. |
| 9,248,042 B2 | * | 2/2016 | Lopez ................... A61F 5/0113 |
| 9,827,131 B2 | | 11/2017 | Watts |
| 11,607,331 B2 | | 3/2023 | Amendola et al. |
| 11,617,672 B2 | | 4/2023 | Ducharme et al. |
| 11,690,747 B1 | | 7/2023 | Amendola et al. |
| 2005/0133044 A1 | | 6/2005 | Goodrich et al. |
| 2009/0143704 A1 | | 6/2009 | Bonneau et al. |
| 2011/0144554 A1 | | 6/2011 | Weaver, II et al. |
| 2014/0288475 A1 | * | 9/2014 | Watts ................... A61F 5/0113 602/27 |
| 2015/0065935 A1 | | 3/2015 | Smith |
| 2017/0367868 A1 | * | 12/2017 | Ducharme ............ A61F 5/0127 |
| 2021/0244558 A1 | * | 8/2021 | Gordon ................ A61F 5/0111 |
| 2022/0313467 A1 | | 10/2022 | Ducharme et al. |
| 2023/0190506 A1 | | 6/2023 | Amendola et al. |

\* cited by examiner

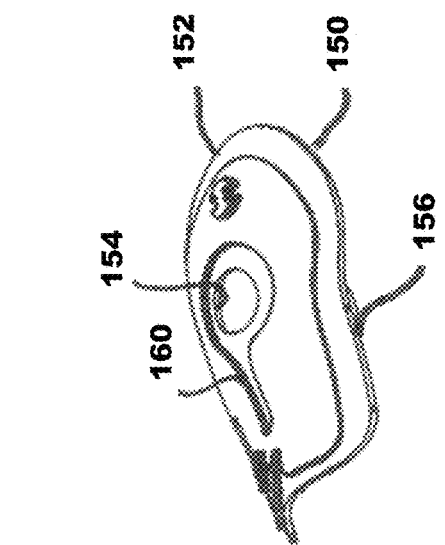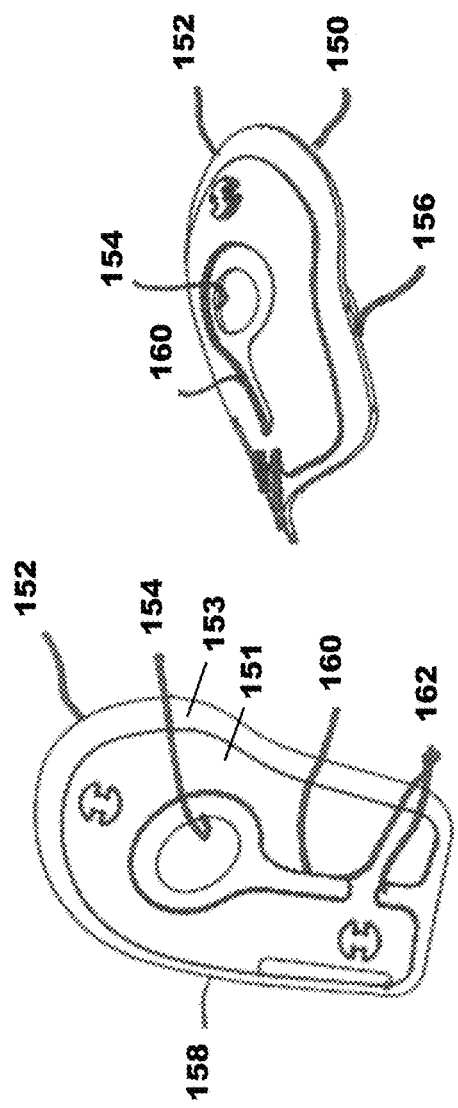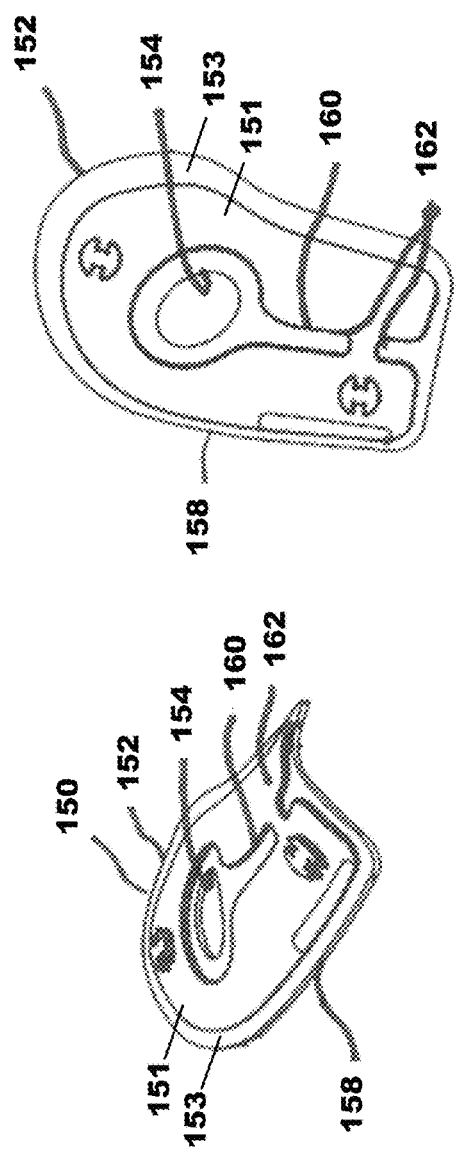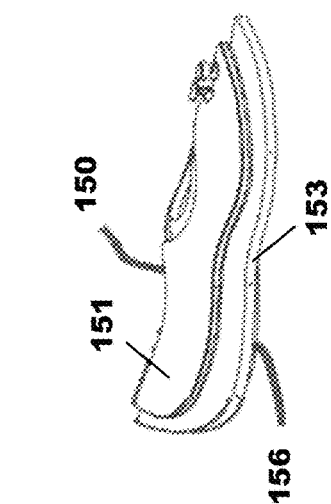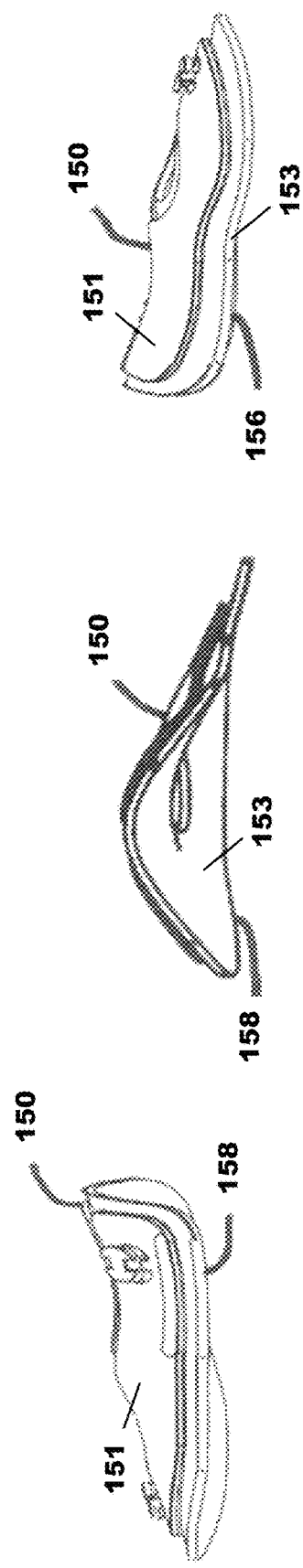

UNIVERSAL DYNAMIC ATHLETIC ANKLE BRACE AND ADD-ON INTERIOR STIRRUP SUPPORT SYSTEM

CROSS-REFERENCE TO RELATED APPLICATION

The present application is a U.S. continuation of, and claims priority under 35 U.S.C. § 120 to, 17/686,388, filed Mar. 3, 2022, which granted as U.S. patent 11,607,331, which '388 application and patent each is incorporated by reference herein, and which '388 application is a nonprovisional patent application of, and claims priority under 35 U.S.C. § 119(e) to, U.S. provisional patent application 63/156,037, filed Mar. 3, 2021, incorporated by reference herein.

COPYRIGHT STATEMENT

Any new and original work of authorship in this document—including the computer program listing—is subject to copyright protection under the copyright laws of the United States and other countries. Reproduction by anyone of this document as it appears in official governmental records is permitted, but otherwise all other copyright rights whatsoever are reserved.

Incorporation of Computer Program Listing Appendix

Submitted concurrently herewith via the USPTO's electronic filing system, and hereby incorporated herein by reference, is a computer program listing appendix representing computer program files including instructions, routines, and/or other contents of several computer programs. A table setting forth the name and size of files included in the computer program listing appendix is included below.

| File Name | Creation Date | File Size (bytes) |
|---|---|---|
| ascify.txt | Mar. 3, 2022 21:46 | 37,473 |
| readme.txt | Mar. 3, 2022 21:46 | 3,978 |
| 1319001.txt | Mar. 3, 2022 21:46 | 24,968,835 |
| 1319002.txt | Mar. 3, 2022 21:46 | 24,968,454 |
| 1319003.txt | Mar. 3, 2022 21:46 | 24,968,073 |
| 1319004.txt | Mar. 3, 2022 21:46 | 9,411,226 |

One of these files, "readme.txt", contains instructions for utilizing "ascify.txt" to convert the other ASCII files in this computer program listing into a compressed ".zip" file. The compressed ".zip" file resulting from "1319.txt" comprises: an interactive PDF file titled "BraceAssembly.pdf" for a three-dimensional rendering of a preferred embodiment of a rear-entry brace in accordance with aspects and features of the invention; three eDrawings illustrating the brace assembly and elastomeric component in accordance with aspects and features of the invention; and a video illustrating a method of donning a preferred embodiment of a rear-entry brace in accordance with aspects and features of the invention. The .PDF file is compatible with the current release of Adobe Acrobat running in Microsoft Windows on a PC; the .EPRT files are compatible with the current release of the free eDrawings viewer program available from Dassault Systemes Corporation running in Microsoft Windows on a PC; and the .MOV file is compatible with Windows Media Player of Microsoft Windows on a PC.

BACKGROUND OF THE INVENTION

Joint sprains are a common occurrence and, in particular, ankle sprains account for an estimated 2 million injuries per year in the United States alone. They occur in nearly all types of daily activities and sporting events and are the most common sports-related injury. A practical method of decreasing the number and severity of these injuries would clearly be of great benefit since ankle sprains result in a risk of further, and even more severe injury and lasting ankle problems, as well as significant time away from games and practices. To this end, many people use prophylactic bracing or ankle taping as a means to decrease the risk of injury, including people who have suffered in the past from a sprained ankle, or in instances where there may be an increased tendency for injury, such as for joints that are subjected to rigorous use or use in uneven terrain; however, while taping is commonly viewed as effective, it is extremely labor intensive, is good for a single use, and requires an educated application, all of which cause it to be very expensive. Rear-entry ankle braces in accordance with aspects and feature of the present invention, which preferably are designed to be worn under shoes, are believed to be an effective alternative to such taping. Moreover, these new and innovative aspects and features are believed to represent further improvements over applicant's other ankle braces as disclosed, for example, in U.S. patent application publication nos. 2017/0135839; 2017/0367868; and 2020/0121486. For purposes of the United States, each of these application publications is incorporated herein by reference.

SUMMARY OF THE INVENTION

The invention includes many aspects and features. Moreover, while many aspects and features relate to, and are described in, the context of ankle braces, aspects and features of the invention are not limited to use only in such context, as will become apparent from the following summaries and detailed descriptions of aspects, features, and one or more embodiments of the invention.

Accordingly, in a first aspect, a rear-entry ankle brace comprises an elastomeric component defining an inside elbow channel configured to span an ankle joint of a wearer, the elastomeric component having: a distal end portion comprising an arched foot portion configured to extend over and cover a top and opposite sides of a mid-foot of the wearer; a proximal end portion comprising an arched leg portion configured to extend over and cover a front and sides of a lower portion of a leg of the wearer; an intermediate portion extending between the foot portion and leg portion and comprising an arched ankle portion configured to extend over and cover a front and sides of an ankle joint of the wearer. Additionally, a channel opening extends along a length of the elastomeric component from the distal end portion to the proximal end portion and enables the elastomeric component to be positioned directly onto and cover the front and sides of the mid-foot, lower leg portion, and ankle joint of the wearer without passing the mid-foot through the proximal end portion. The brace further comprises one or more straps for adjustably tensioning first and second rear edges of the channel opening in an area of the leg portion toward one another and securing the leg portion to the lower leg of the wearer; and one or more straps for adjustably tensioning first and second bottom edges of the channel opening in an area of the foot portion toward one another and securing the foot portion to the mid-foot of the wearer.

In another aspect, a rear-entry ankle brace comprises an elastomeric component defining an inside elbow channel configured to span an ankle joint of a wearer, the elastomeric component having: a distal end portion comprising an arched foot portion configured to extend over and cover a top and opposite sides of a mid-foot of the wearer; a proximal end portion comprising an arched leg portion configured to extend over and cover a front and sides of a lower portion of a leg of the wearer; and an intermediate portion extending between the foot portion and leg portion and comprising an arched ankle portion configured to extend over and cover a front and sides of an ankle joint of the wearer. A channel opening extends along a length of the elastomeric component from the distal end portion to the proximal end portion and enables the elastomeric component to be positioned directly onto and cover the front and sides of the mid-foot, lower leg portion, and ankle joint of the wearer without passing the mid-foot through the proximal end portion. The brace further comprises a first leg strap secured to a first rear edge of the channel opening in an area of the leg portion and a second leg strap connected to a second rear edge of the channel opening in the area of the leg portion, the first and second leg straps configured to removably attach to each other for tensioning the first and second rear edges toward one another and securing the leg portion to the lower leg of the wearer; and a first foot strap extending from a first bottom edge of the channel opening an the area of the foot portion and a second foot strap extending from a second bottom edge of the channel opening in the area of the foot portion, each of the first and second leg straps configured to span the channel opening in the area of the foot portion, and to removably attach to at least one of the first and second leg straps when removably attached to each other for tensioning the first and second bottom edges toward one another and securing the foot portion to the mid-foot of the wearer.

The first and second leg straps preferably span the channel opening between the first and second rear edges and overlap one another, and the brace preferably further comprises a slot along one of the first and second rear edges of the channel opening in the area of the leg portion through which one of the first and second leg straps extends. The slot preferably is defined by a D-ring that is at least partially embedded within the elastomeric component.

In a feature, the first and second foot straps extend diagonally upward from the first and second bottom edges of the channel opening and cross over each other along the intermediate portion of the elastomeric component when the first and second foot straps are removably attached to at least one of the first and second leg straps for tensioning the first and second bottom edges toward one another and securing the foot portion to the mid-foot of the wearer.

In a feature, one of the first and second foot straps is a lower foot strap that extends under the other of the first and second foot straps that is an upper foot strap, the lower foot strap forming a plantar surface of the brace when spanning the channel opening in the area of the foot portion. The upper foot strap preferably extends through a slot along one of the first and second bottom edges of the channel opening in the area of the foot portion, and the slot preferably is defined by a D-ring that is at least partially embedded within the elastomeric component.

In another aspect, a rear-entry ankle brace comprises an elastomeric component defining an inside elbow channel configured to span an ankle joint of a wearer, the elastomeric component having: a distal end portion comprising an arched foot portion configured to extend over and cover a top and opposite sides of a mid-foot of the wearer; a proximal end portion comprising an arched leg portion configured to extend over and cover a front and sides of a lower portion of a leg of the wearer; and an intermediate portion extending between the foot portion and leg portion and comprising an arched ankle portion configured to extend over and cover a front and sides of an ankle joint of the wearer. A channel opening extends along a length of the elastomeric component from the distal end portion to the proximal end portion and enables the elastomeric component to be positioned directly onto and cover the front and sides of the mid-foot, lower leg portion, and ankle joint of the wearer without passing the mid-foot through the proximal end portion. The brace further comprises a leg strap secured to a rear edge of the channel opening in an area of the leg portion and configured to attach to a second rear edge of the channel opening in the area of the leg portion removably attach to itself for tensioning the first and second rear edges toward one another and securing the leg portion to the lower leg of the wearer; and a first foot strap secured to and extending from a first bottom edge of the channel opening in an area of the foot portion and a second foot strap secured to and extending from a second bottom edge of the channel opening in the area of the foot portion, each of the first and second leg straps configured to span the channel opening in the area of the foot portion, and to removably attach to the leg strap for tensioning the first and second bottom edges toward one another and securing the foot portion to the mid-foot of the wearer.

In a feature, the leg strap twice spans the channel opening between the first and second rear edges and overlaps itself, and wherein the brace further comprises a slot along one of the first and second rear edges of the channel opening in the area of the leg portion through which the leg strap extends. The slot preferably is defined by a D-ring that is at least partially embedded within the elastomeric component.

In a feature, the first and second foot straps extend diagonally upward from the first and second bottom edges of the channel opening and cross over each other along the intermediate portion of the elastomeric component when the first and second foot straps are removably attached to the leg strap for tensioning the first and second bottom edges toward one another and securing the foot portion to the mid-foot of the wearer.

In a feature, one of the first and second foot straps is a lower foot strap that extends under the other of the first and second foot straps that is an upper foot strap, the lower foot strap forming a plantar surface of the brace when spanning the channel opening in the area of the foot portion.

The upper foot strap preferably extends through a slot along one of the first and second bottom edges of the channel opening in the area of the foot portion, and the slot preferably is defined by a D-ring that is at least partially embedded within the elastomeric component.

In a feature, each said strap is removably attached to another said strap using hook and loop fasteners.

In another aspect, a rear-entry ankle brace comprises an elastomeric component defining an inside elbow channel configured to span an ankle joint of a wearer, the elastomeric component having: a distal end portion comprising an arched foot portion configured to extend over and cover a top and opposite sides of a mid-foot of the wearer; a proximal end portion comprising an arched leg portion configured to extend over and cover a front and sides of a lower portion of a leg of the wearer; and an intermediate portion extending between the foot portion and leg portion and comprising an arched ankle portion configured to extend over and cover a front and sides of an ankle joint of the wearer. A channel opening extends along a length of the elastomeric component from the distal end portion to the proximal end portion and enables the elastomeric component to be positioned directly onto and cover the front and sides of the mid-foot, lower leg portion, and ankle joint of the wearer without passing the mid-foot through the proximal end portion. The brace further comprises means for adjustably tensioning first and second rear edges of the channel opening in an area of the leg portion toward one another and securing the leg portion to the lower leg of the wearer; and means for adjustably tensioning first and second bottom edges of the channel opening in an area of the foot portion toward one another and securing the foot portion to the mid-foot of the wearer.

In a feature, the elastomeric component consists of a single molded piece of one or more thermoplastic materials.

In a feature, the elastomeric component further defines on each of opposite lateral and medial sides of the brace a central hub with radiating struts extending from the central hub and with interstitial areas extending between the radiating struts.

The interstitial areas preferably comprises areas that are substantially thinner than the radiating struts and that include perforations extending through the elastomeric for breathability of the brace when worn. Additionally, one or more of the radiating struts preferably comprises a thickness of from 1 mm to 10 mm, a width of from 3 mm to 20 mm, and a durometer of from 10 to 140 on the Shore A scale.

In a feature, elastomeric component is symmetrical relative to a plane and is adapted to be used on either a right ankle or a left ankle.

In a feature, the brace further comprises a pair of stirrups, each attached to an inner side of the elastomeric component in opposing relation to each other and each contoured so as to receive a respective malleolus of the wearer, the pair of stirrups acting as stiffening ribs in the anatomic orientation of the lateral collateral ligamentous complex of the ankle joint.

In another aspect, a method comprises steps for donning a rear-entry ankle brace, the brace comprising an elastomeric component defining an inside elbow channel configured to span an ankle joint of a wearer, the elastomeric component having a distal end portion comprising an arched foot portion configured to extend over and cover a top and opposite sides of a mid-foot of the wearer; a proximal end portion comprising an arched leg portion configured to extend over and cover a front and sides of a lower portion of a leg of the wearer; and an intermediate portion extending between the foot portion and leg portion and comprising an arched ankle portion configured to extend over and cover a front and sides of an ankle joint of the wearer. A channel opening extends along a length of the elastomeric component from the distal end portion to the proximal end portion and enables the elastomeric component to be positioned directly onto and cover the front and sides of the mid-foot, lower leg portion, and ankle joint of the wearer without passing the mid-foot through the proximal end portion. The brace further comprises one or more leg straps for tensioning first and second rear edges of the channel opening in an area of the leg portion toward one another and securing the leg portion to the lower leg of the wearer; and two foot straps for tensioning first and second bottom edges of the channel opening in an area of the foot portion toward one another and securing the foot portion to the mid-foot of the wearer. In this context, the steps of the method comprise: positioning the elastomeric component directly onto and in covering relation with the front and sides of the mid-foot, lower leg portion, and ankle joint of the wearer without passing the elastomeric component over the toes of the foot; tensioning the first and second bottom edges of the channel opening in the area of the foot portion toward one another by pulling the two foot straps and then stepping on the overlapping portions of the foot straps to hold the tension; bending a knee of the leg of the wearer over at least the mid-foot of the wearer to tension the elastomeric component and preload the brace; pulling and securing the one or more leg straps to tension the first and second rear edges of the channel opening toward one another and secure the leg portion to the lower leg of the wearer; and ceasing the stepping on the overlapping portions of the foot straps and separately pulling and securing each of the foot straps to one of the one or more leg straps to selectively tension the first and second bottom edges of the channel opening toward one another and secure the foot portion to the mid-foot of the wearer.

In a feature, the step of positioning the elastomeric component directly onto and in covering relation with the front and sides of the mid-foot, lower leg portion, and ankle joint of the wearer comprises positioning the elastomeric component such that each of the central hubs aligns with a respective malleolus.

In a feature, the rear-entry ankle brace further comprises a pair of stirrups, each attached to an inner side of the elastomeric component in opposing relation to each other and each contoured so as to receive a respective malleolus of the wearer. The step of positioning the elastomeric component directly onto and in covering relation with the front and sides of the mid-foot, lower leg portion, and ankle joint of the wearer preferably comprises positioning the elastomeric component such that each of the stirrups receives a respective malleolus of the wearer. Additionally, the method preferably further comprises a preliminary step of removably attaching each of the pair of stirrups to the elastomeric component before said positioning of the elastomeric component.

In a feature, the method further comprises donning a shoe while the brace is being worn, with the leg portion extending above the shoe and the foot portion being received within the shoe.

In another aspect, an ankle brace to be worn under the shoe of a wearer comprises an elastomeric component being open to the bottom and forming a first arched foot portion along a medial foot axis with opposing bottom edges so as to accommodate the top of a mid-foot of the wearer, and forming a second arched leg portion along a medial leg axis with opposing rear edges so as to accommodate the front of the lower leg of the wearer. The medial axis of the foot portion forms an angle to the medial axis of the leg portion. The elastomeric component comprise a pair of opposing support systems each formed by an interlinking network of band members having a central hub and radiating struts, with interstitial spaces extending between the band members including a flat web of breathable material. The elastomeric component preferably has a configuration with mirror symmetry about a medial plane formed at the intersection of the medial axis of the foot portion and the medial axis of the leg portion. At least one foot strap extends from a first bottom edge of the foot portion and a second foot strap extends from a second bottom edge of the foot portion and cooperates with the first foot strap to close the foot portion and form a plantar surface of the ankle; and at least one leg strap closes the leg portion about the lower leg of the wearer.

In a feature, the brace is dynamic so as store and rebalance energy by allowing pivoting motion between the foot portion and the leg portion but inhibiting lateral and medial translational or pivotal motion about an axis perpendicular to the transverse axis along the length of the foot between the foot portion and the leg portion In a feature, the elastomeric component is formed by molding or casting.

In a feature, the brace further comprises a pair of foot straps with a first foot strap extending from a first bottom edge of the foot portion and a second foot strap extending from a second bottom edge of the foot portion which cooperating to form the plantar surface of the ankle brace. Preferably, one foot strap crosses under the other foot strap; and preferably one foot strap is connected to the bottom of the elastomeric component with an opening that receives the other foot strap to allow for the cooperation of the foot straps. One foot strap may be connected to the bottom of the elastomeric component with a D-ring and the opening may be a slot along the length of the D-ring.

Additional aspects and features are disclosed in the computer program listing and in the incorporated references.

In addition to the aforementioned aspects and features of the invention, it should be noted that the invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the invention now will be described in detail with reference to the accompanying drawings.

FIG. 16 is a perspective view of a front of a preferred stirrup of a rear-entry ankle brace in accordance with one or more aspects and features of the present invention.

FIG. 17 is a front elevational view of the stirrup of FIG. 16.

FIG. 18 is another perspective view of the front of the stirrup of FIG. 16.

FIG. 19 is a first side elevational view of the stirrup of FIG. 16.

FIG. 20 is a top plan view of the stirrup of FIG. 16.

FIG. 21 is a second side elevational view of the stirrup of FIG. 16.

DETAILED DESCRIPTION

Figure 1:
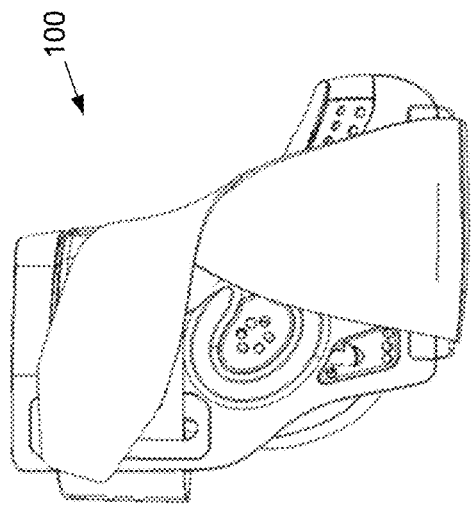
FIG. 1 is a front elevational view of a preferred rear-entry ankle brace in accordance with one or more aspects and features of the present invention.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once but not necessarily every time during performance of the claimed method.

Furthermore, it is important to note that, as used herein, "comprising" is open-ended insofar as that which follows such term is not exclusive. Additionally, "a" and "an" each generally denotes "at least one" but does not exclude a plurality unless the contextual use dictates otherwise. Thus, reference to "a picnic basket having an apple" is the same as "a picnic basket comprising an apple" and "a picnic basket including an apple", each of which identically describes "a picnic basket having at least one apple" as well as "a picnic basket having apples"; the picnic basket further may contain one or more other items beside an apple. In contrast, reference to "a picnic basket having a single apple" describes "a picnic basket having only one apple"; the picnic basket further may contain one or more other items beside an apple. In contrast, "a picnic basket consisting of an apple" has only a single item contained therein, i.e., one apple; the picnic basket contains no other item.

When used herein to join a list of items, "or" denotes "at least one of the items" but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers"; the picnic basket further may contain one or more other items beside cheese and crackers.

When used herein to join a list of items, "and" denotes "all of the items of the list". Thus, reference to "a picnic basket having cheese and crackers" describes "a picnic basket having cheese, wherein the picnic basket further has crackers", as well as describes "a picnic basket having crackers, wherein the picnic basket further has cheese"; the picnic basket further may contain one or more other items beside cheese and crackers.

The phrase "at least one" followed by a list of items joined by "and" denotes an item of the list but does not require every item of the list. Thus, "at least one of an apple and an orange" encompasses the following mutually exclusive scenarios: there is an apple but no orange; there is an orange but no apple; and there is both an apple and an orange. In these scenarios if there is an apple, there may be more than one apple, and if there is an orange, there may be more than one orange. Moreover, the phrase "one or more" followed by a list of items joined by "and" is the equivalent of "at least one" followed by the list of items joined by "and".

Referring now to the drawings, one or more preferred embodiments of the invention are next described. The following description of one or more preferred embodiments is merely exemplary in nature and is in no way intended to limit the invention, its implementations, or uses.

Figure 2:
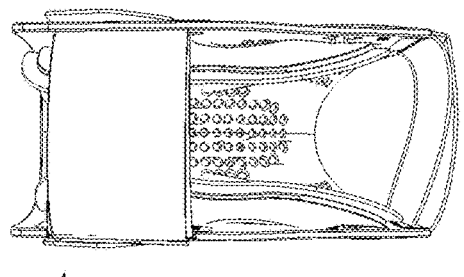
FIG. 2 is a rear elevational view of the rear-entry ankle brace of FIG. 1.
Figure 3:
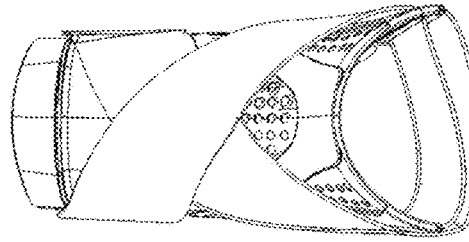
FIG. 3 is a first side elevational view of the rear-entry ankle brace of FIG. 1.
Figure 4:
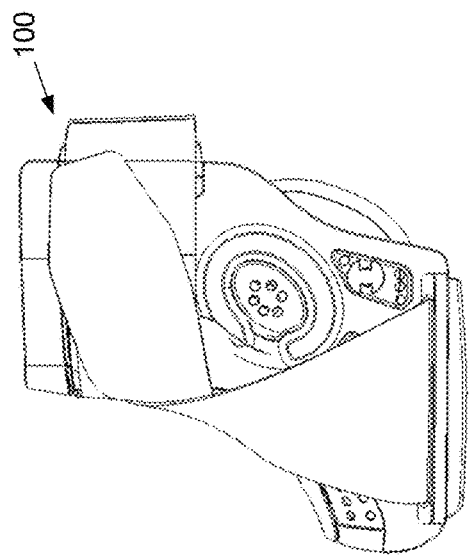
FIG. 4 is a top plan view of the rear-entry ankle brace of FIG. 1.
Figure 5:
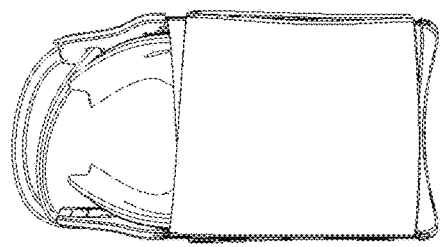
FIG. 5 is a bottom plan view of the rear-entry ankle brace of FIG. 1.
Figure 6:
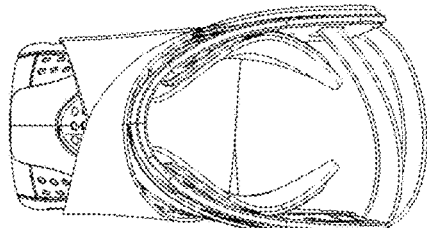
FIG. 6 is a second, opposite side elevational view of the rear-entry ankle brace of FIG. 1.

Specifically, a front elevational view of a preferred rear-entry ankle brace 100 in accordance with one or more aspects and features of the present invention is illustrated in FIG. 1. Additionally, FIG. 2 is a rear elevational view of the rear-entry ankle brace 100; FIG. 3 is a first side elevational view of the rear-entry ankle brace 100; FIG. 4 is a top plan view of the rear-entry ankle brace 100; FIG. 5 is a bottom plan view of the rear-entry ankle brace 100; and FIG. 6 is a second, opposite side elevational view of the rear-entry ankle brace 100.

Figure 7:
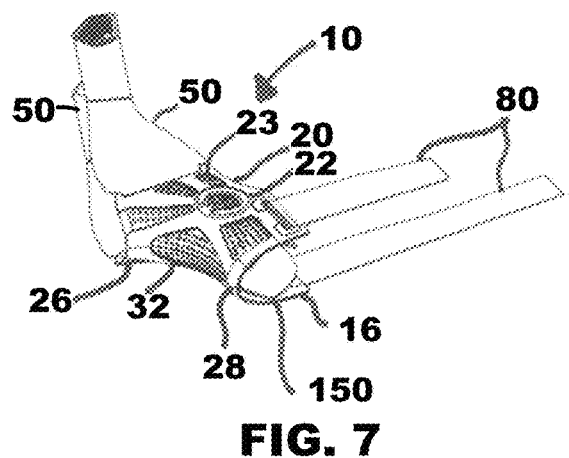
FIG. 7 is a first perspective of another preferred rear-entry ankle brace in accordance with one or more aspects and features of the present invention.
Figure 10:
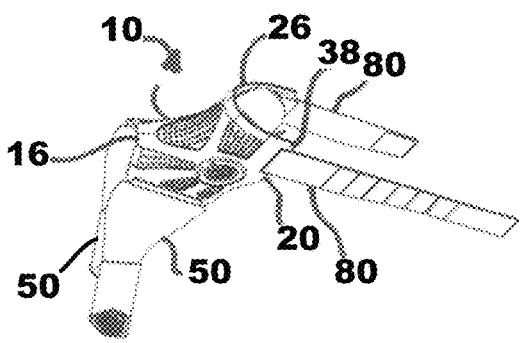
FIG. 10 is a third perspective of the rear-entry ankle brace of FIG. 7.
Figure 8:
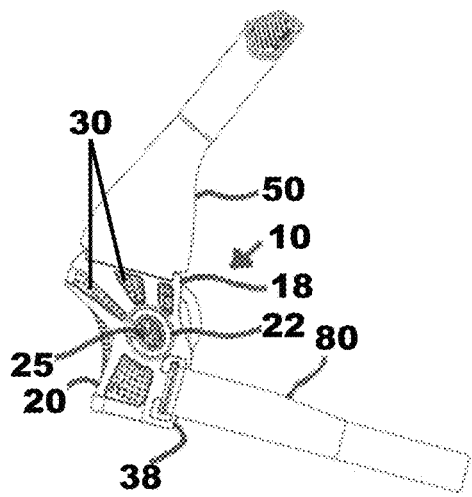
FIG. 8 is a first side elevational view of the rear-entry ankle brace of FIG. 7.
Figure 11:
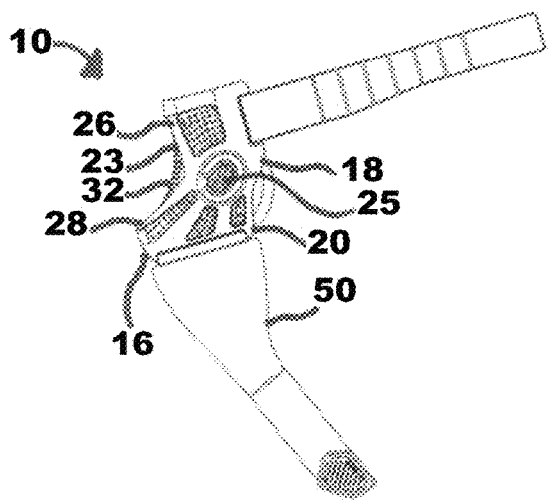
FIG. 11 is a second side elevational view of the rear-entry ankle brace of FIG. 7.
Figure 9:
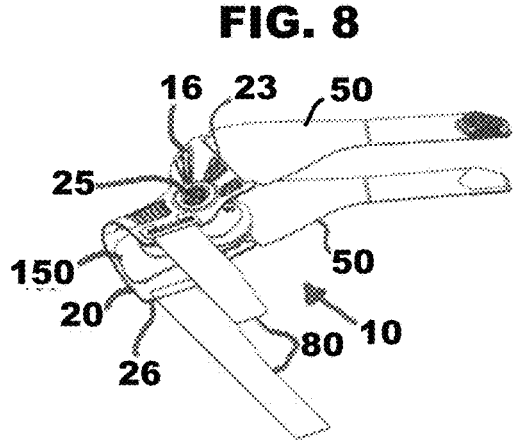
FIG. 9 is a second perspective of the rear-entry ankle brace of FIG. 7.
Figure 12:
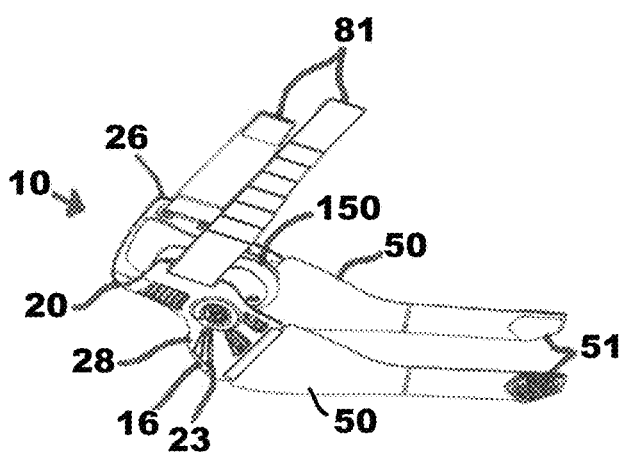
FIG. 12 is a fourth perspective of the rear-entry ankle brace of FIG. 7.
Figure 13:
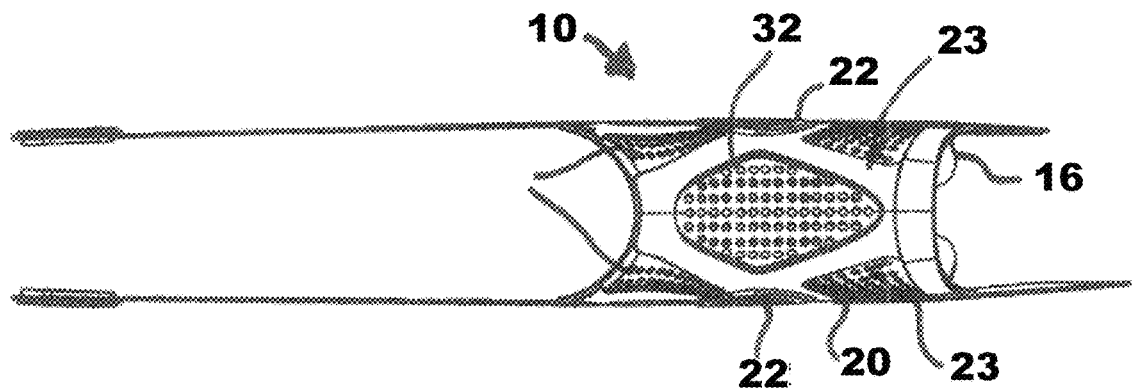
FIG. 13 is a front elevational view of the rear-entry ankle brace of FIG. 7.
Figure 14:
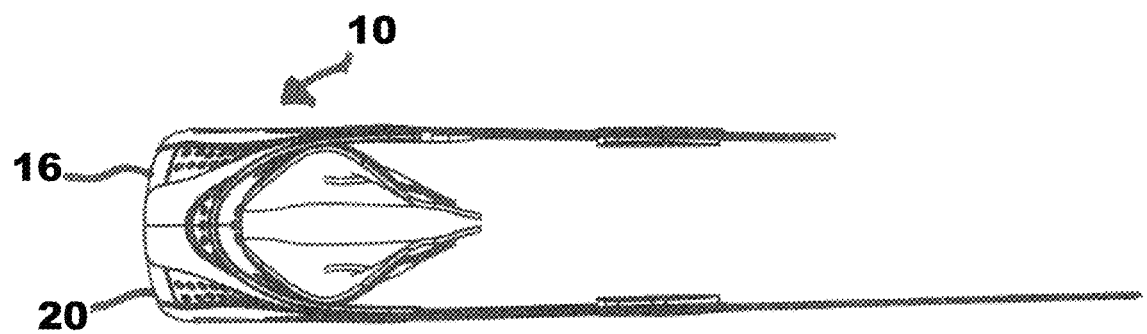
FIG. 14 is a top plan of the rear-entry ankle brace of FIG. 7.
Figure 15:
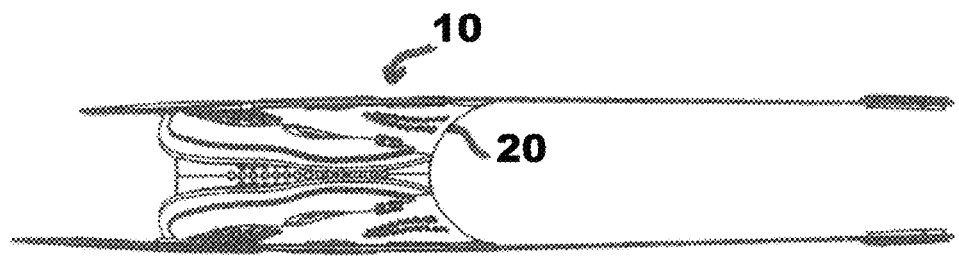
FIG. 15 is a back elevational view of the rear-entry ankle brace of FIG. 7.

With respect to another preferred rear-entry ankle brace 10 in accordance with one or more aspects and features of the present invention, FIG. 7 is a first perspective view of the ankle brace 10. Additionally, FIG. 8 is a first side elevational view of the rear-entry ankle brace 10; FIG. 9 is a second perspective of the rear-entry ankle brace 10; FIG. 10 is a third perspective of the rear-entry ankle brace 10; FIG. 11 is a second side elevational view of the rear-entry ankle brace 10; FIG. 12 is a fourth perspective of the rear-entry ankle brace 10; FIG. 13 is a front elevational view of the rear-entry ankle brace 10; FIG. 14 is a top plan of the rear-entry ankle brace 10; and FIG. 15 is a back elevational view of the rear-entry ankle brace 10.

The rear-entry ankle braces 100 and 10 each are shown with a pair of optional stirrups 150 that serve to stabilize the brace in use. Additionally, FIG. 17 is a front elevational view of a said stirrup 150; FIG. 18 is another perspective view of the front of the stirrup 150; FIG. 19 is a first side elevational view of the stirrup 150; FIG. 20 is a top plan view of the stirrup 150; and FIG. 21 is a second side elevational view of the stirrup 150.

Each stirrup 150 is removably attached to an inside of the elastomeric component with the pair of stirrups being arranged in opposing facing relation to each other. Each stirrup 150 further comprises a contoured surface that is designed to receive a respective malleolus, and each stirrup 150 preferably comprises a molded, rigid component 151 that provides stiffness to the elastomeric component and a foam component 153 for comfort of the wearer.

Figure 22:
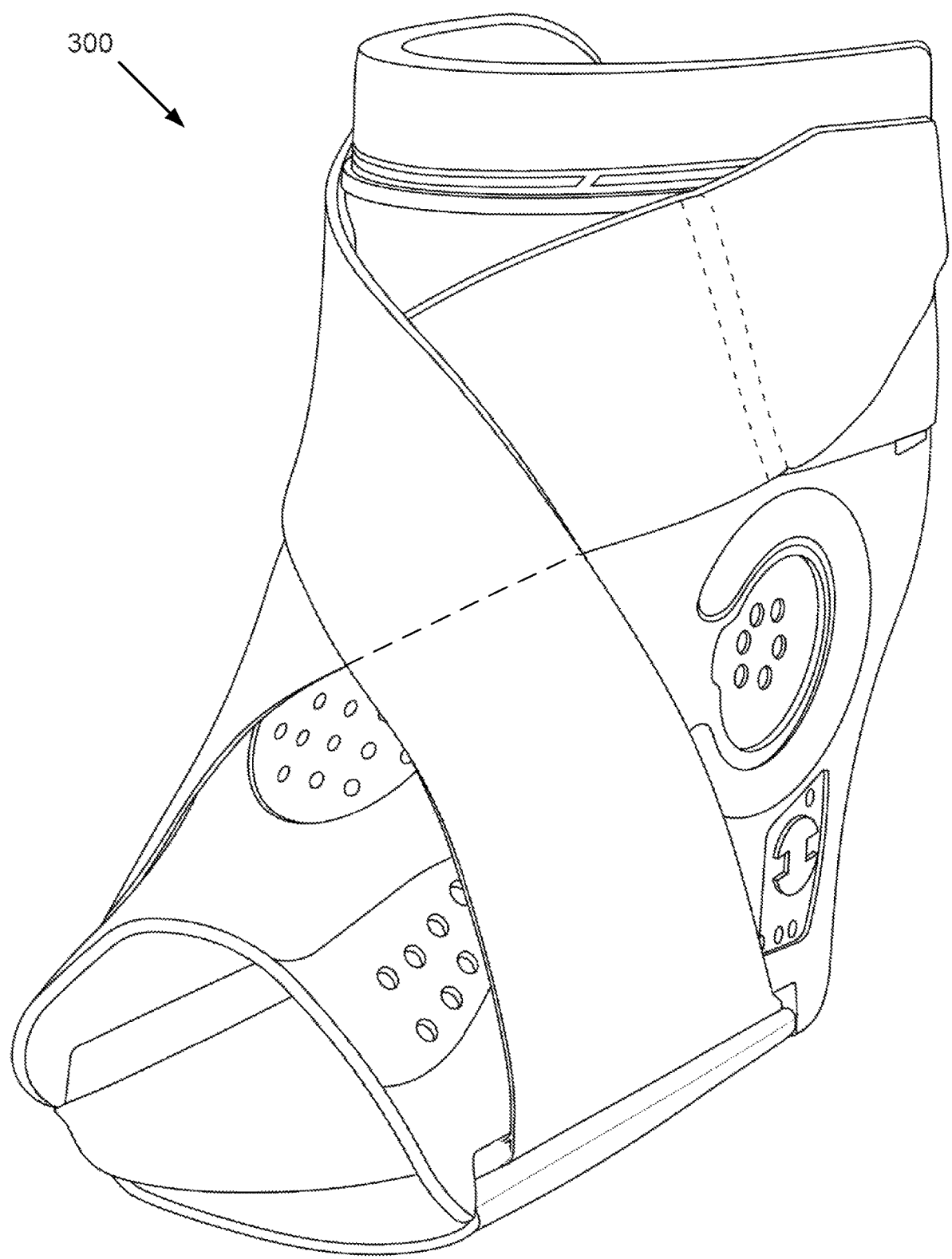
FIG. 22 is a perspective view of a front of another preferred rear-entry ankle brace in accordance with one or more aspects and features of the present invention.
Figure 23:
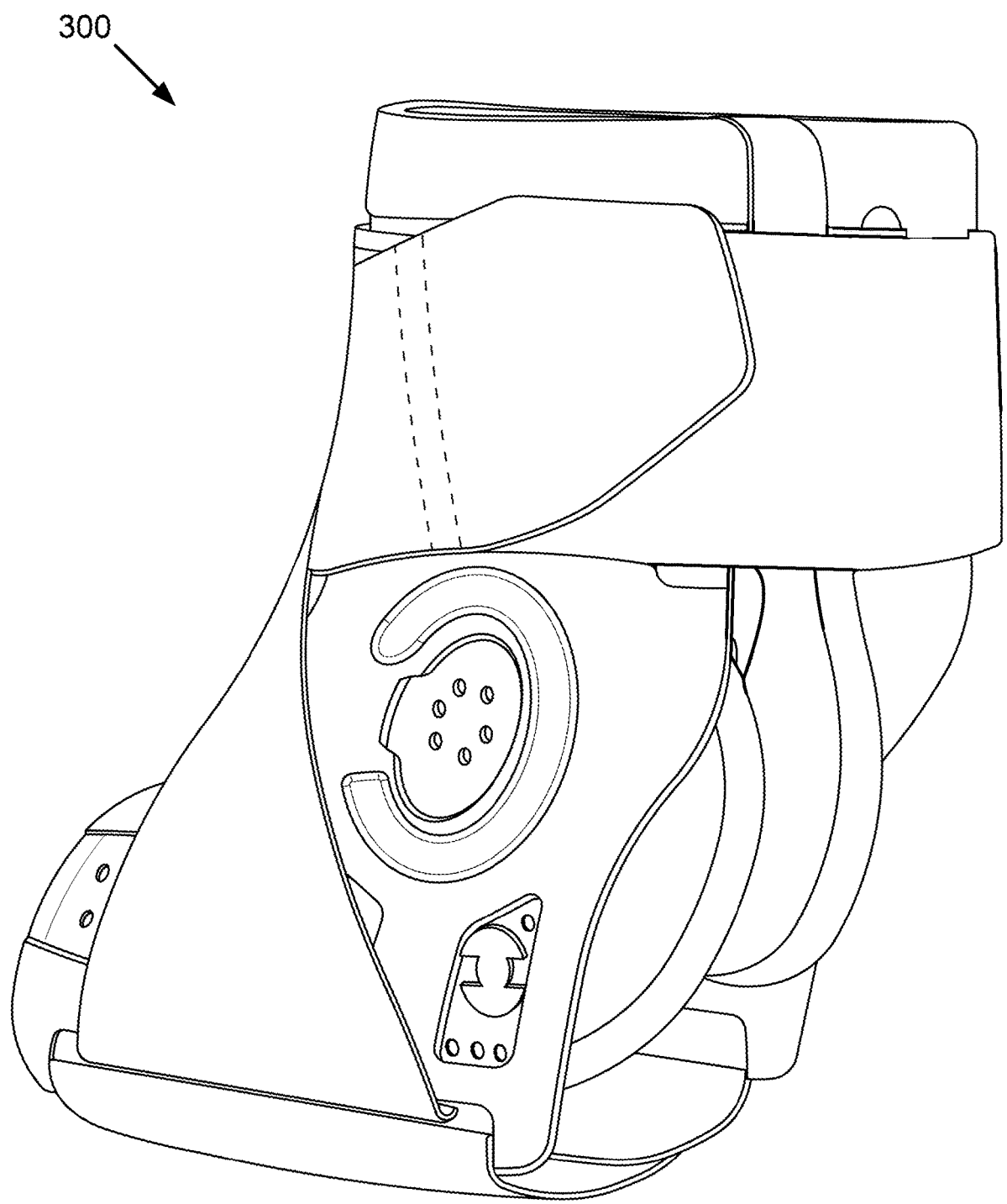
FIG. 23 is a perspective view of a rear of the rear-entry ankle brace of FIG. 22.
Figure 24:
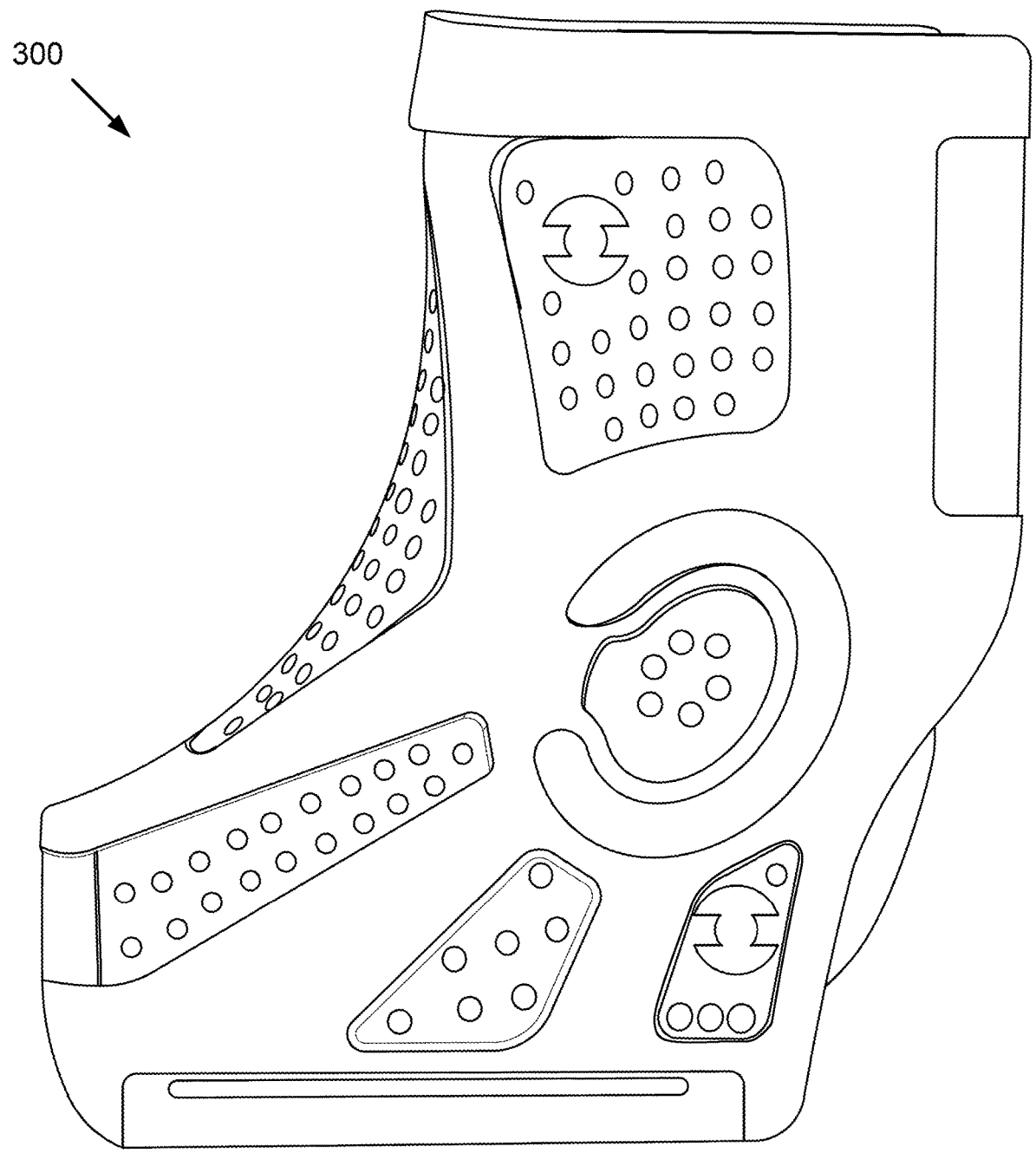
FIG. 24 is a side elevational view of the rear-entry ankle brace of FIG. 22 in which the straps are omitted.
Figure 25:
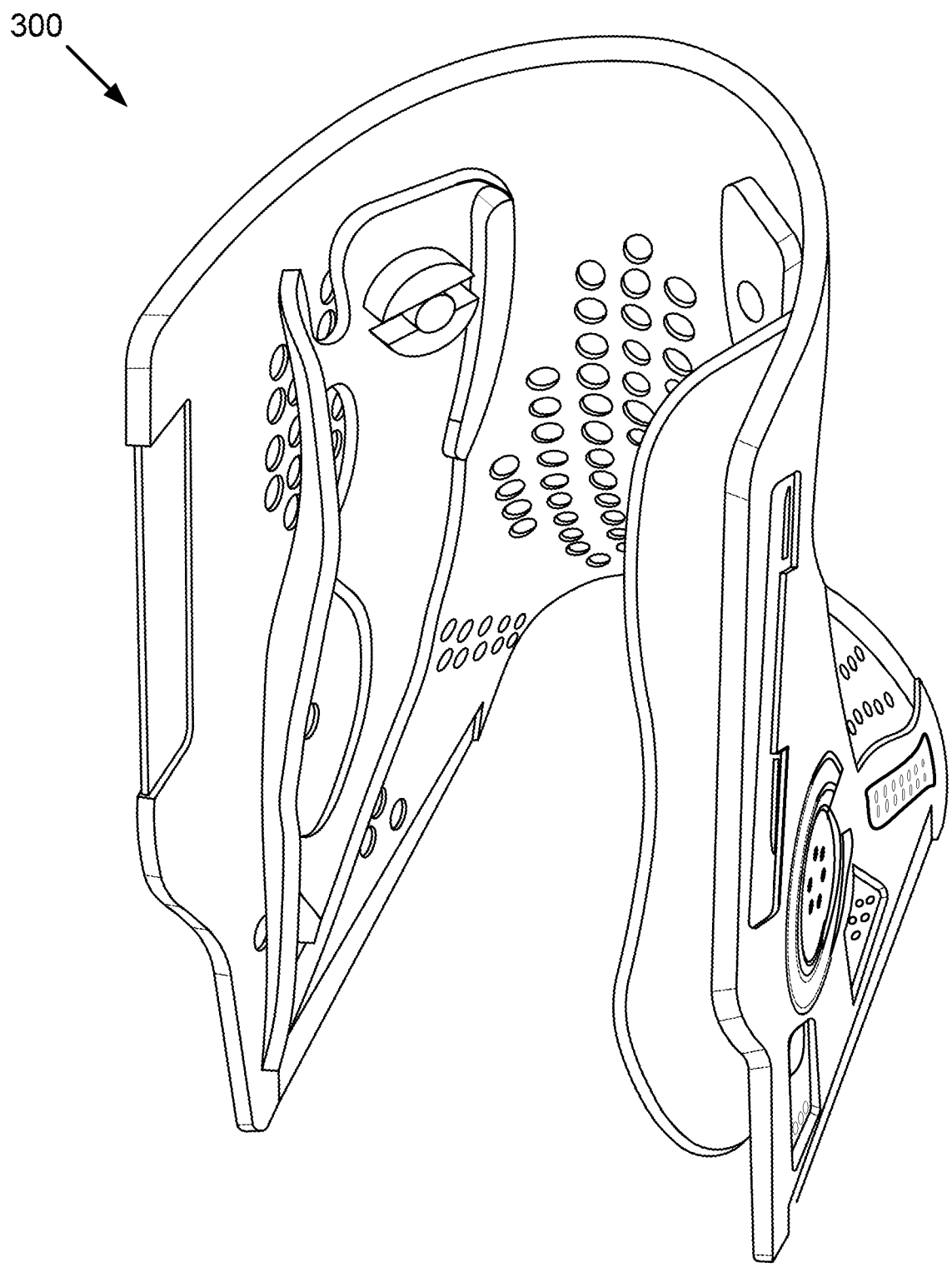
FIG. 25 is a perspective view of a rear of the rear-entry ankle brace of FIG. 24.

Yet another preferred rear-entry ankle brace 300 in accordance with one or more aspects and features of the present invention is illustrated in FIGS. 22-25. Specifically, FIG. 22 is a first perspective view of a front of another preferred rear-entry ankle brace 300; FIG. 23 is a perspective view of a rear of the rear-entry ankle brace 300; FIG. 24 is a side elevational view of the rear-entry ankle brace 300 in which the straps are omitted; and FIG. 25 is a perspective view of a rear of the rear-entry ankle brace 300.

Figure 28:
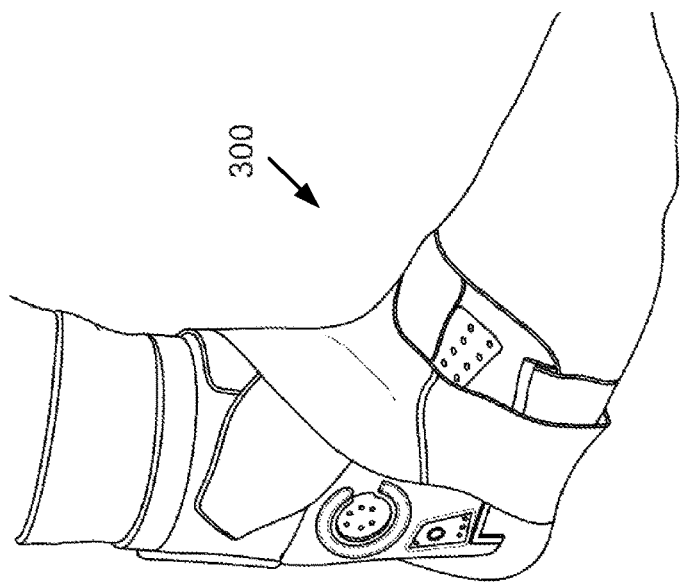
FIG. 28 is a perspective view of the lateral side of the rear-entry ankle brace of FIG. 26.
Figure 27:
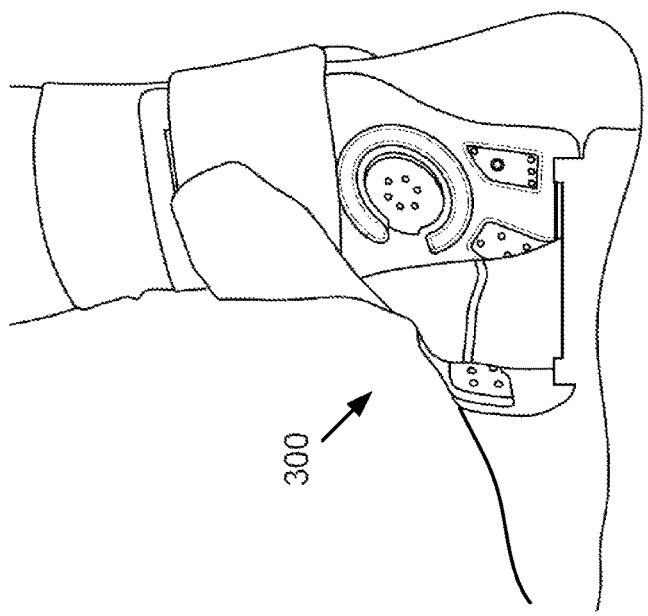
FIG. 27 is a perspective view of the medial side of the rear-entry ankle brace of FIG. 26.
Figure 26:
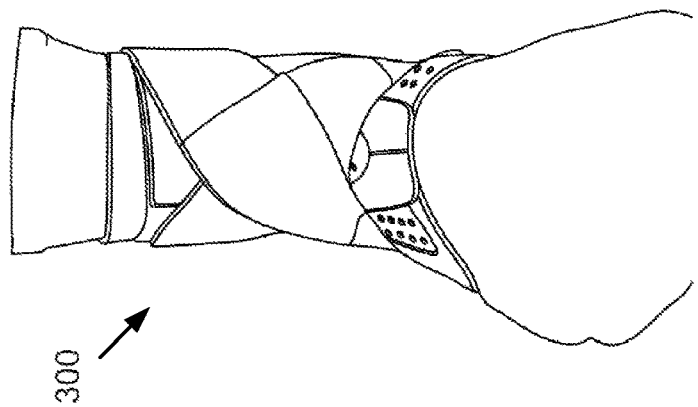
FIG. 26 is perspective view of a front of a rear-entry ankle brace of FIG. 22 being worn in support of the ankle of a right leg of a wearer.
Figure 31:
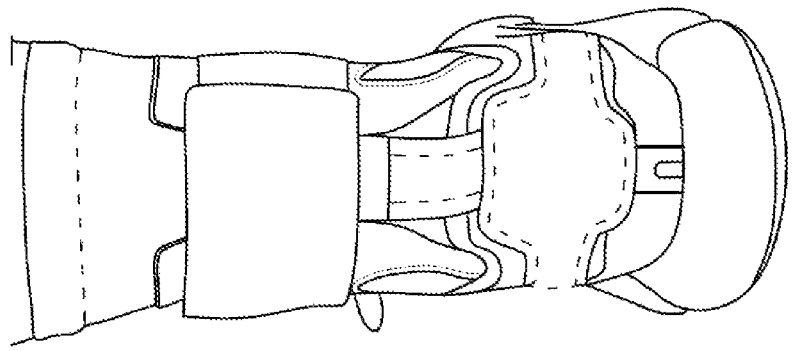
FIG. 31 is a perspective view of the rear of the rear-entry ankle brace of FIG. 29 being worn under a shoe.
Figure 30:
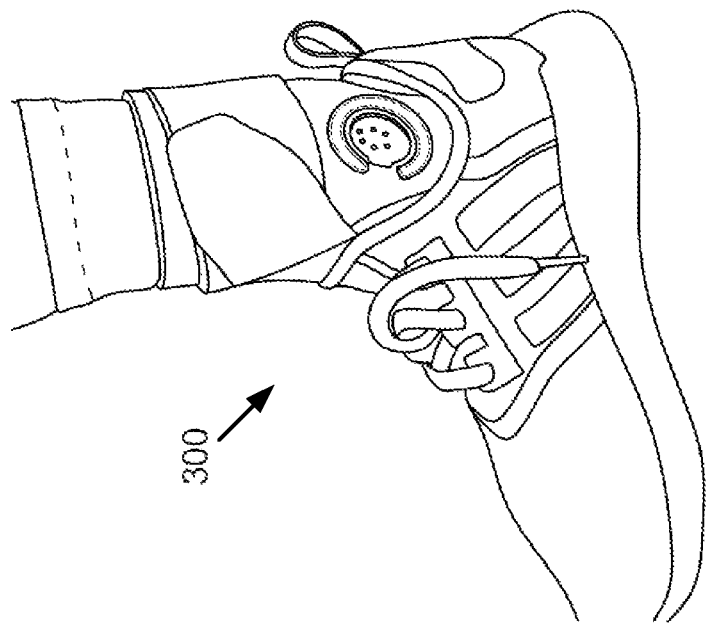
FIG. 30 is a perspective view of the medial side of the rear-entry ankle brace of FIG. 29 being worn under a shoe.
Figure 29:
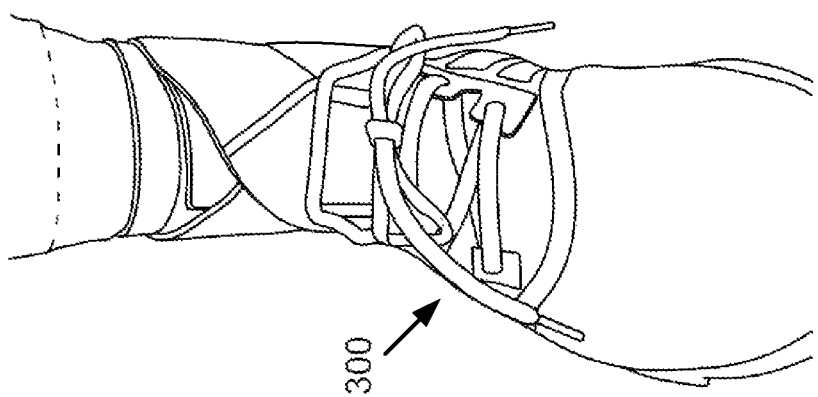
FIG. 29 is a perspective view of the rear-entry ankle brace of FIG. 22 being worn under a shoe.

Braces of preferred embodiments of the invention are intended to be work under shoes. In this respect, FIGS. 26-28 show the brace 300 after being donned by a wearer, and FIGS. 29-31 show the subsequent use of the brace 300 by the wearer after donning a shoe. Specifically, FIG. 26 is perspective view of a front of the rear-entry ankle brace 300 being worn in support of the ankle of a right leg of the wearer; FIG. 27 is a perspective view of the medial side of the rear-entry ankle brace 300; and FIG. 28 is a perspective view of the lateral side of the rear-entry ankle brace 300. FIG. 29 is a perspective view of the rear-entry ankle brace 300 being worn under a shoe; FIG. 30 is a perspective view of the medial side of the rear-entry ankle brace 300 being worn under a shoe; and FIG. 31 is a perspective view of the rear of the rear-entry ankle brace 300 being worn under a shoe.

Figure 32:
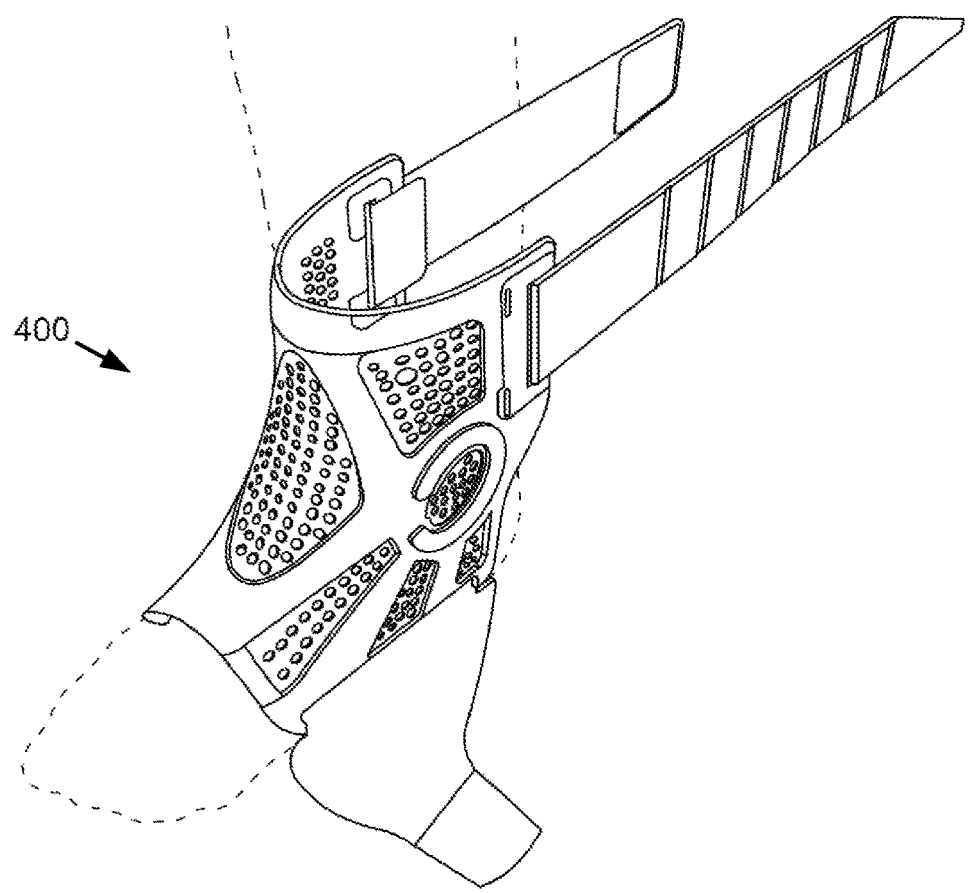
FIG. 32 is a perspective view of an alternative preferred rear-entry ankle brace in accordance with one or more aspects and features of the present invention, wherein the brace does not include the optional stirrups.

FIG. 32 is a perspective view of an alternative preferred rear-entry ankle brace 400 in accordance with one or more aspects and features of the present invention, wherein the brace 400 is shown without optional stirrups 150.

Figure 33:
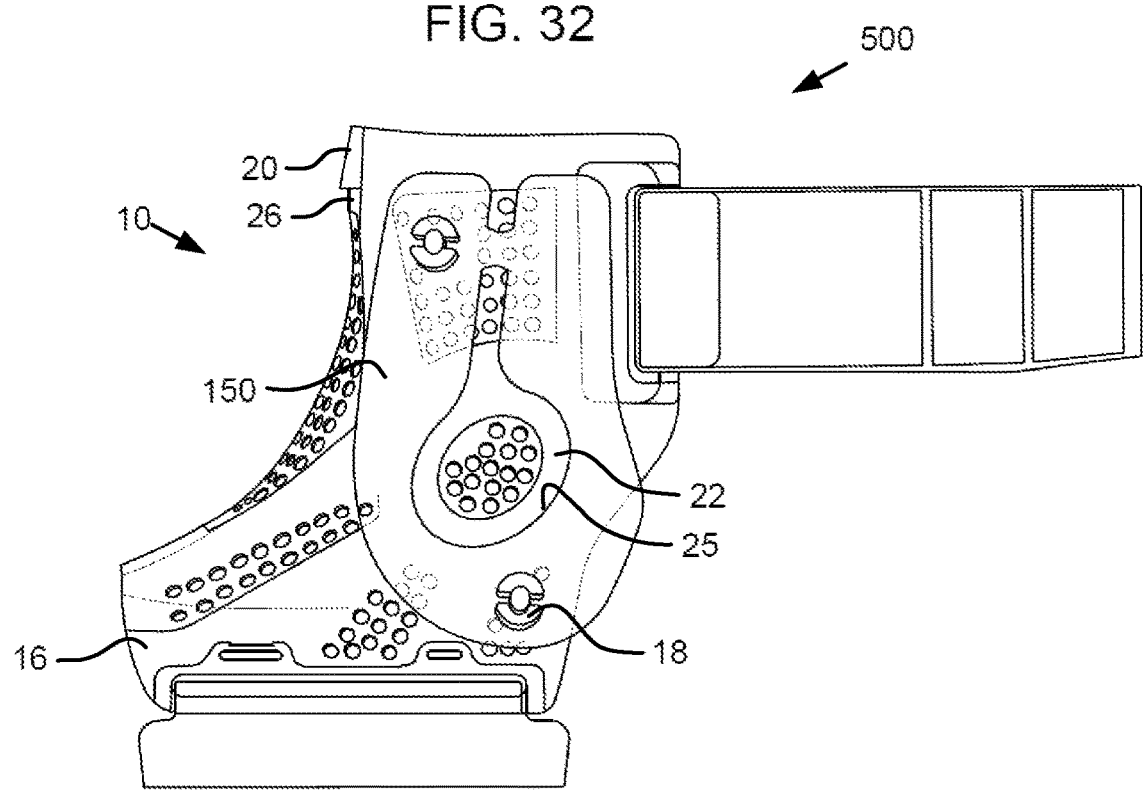
FIG. 33 is a side elevational view of another preferred rear-entry ankle brace in accordance with one or more aspects and features of the present invention, wherein the elastomeric component is rendered transparent for better illustration of a stirrup that is attached to an inner side of the elastomeric component.

FIG. 33 is a side elevational view of another preferred rear-entry ankle brace 500 in accordance with one or more aspects and features of the present invention, wherein the elastomeric component is rendered transparent for better illustration of a stirrup 150 that is attached to an inner side of the elastomeric component.

Figure 34:
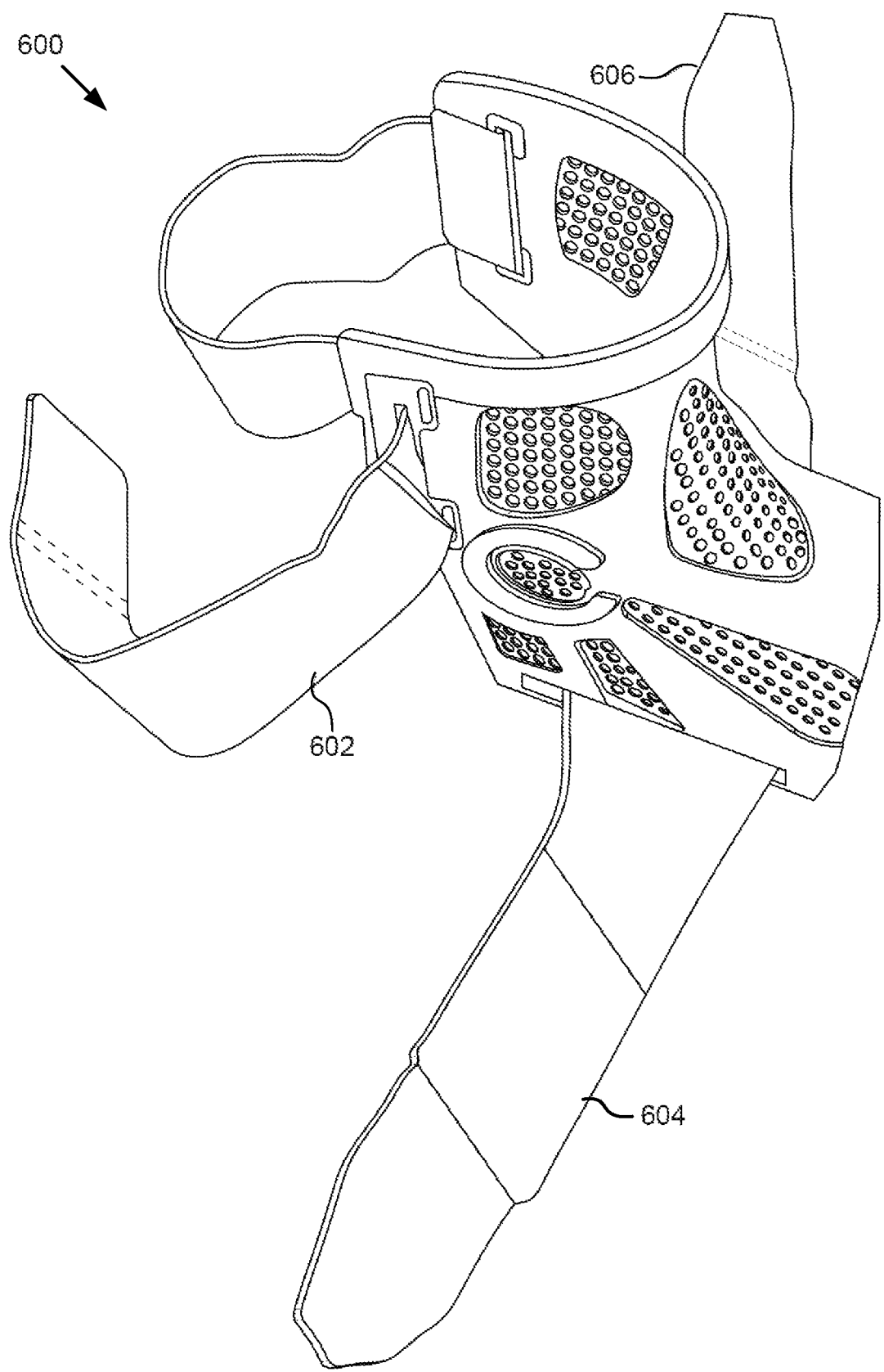
FIG. 34 is a perspective view of another preferred rear-entry ankle brace in accordance with one or more aspects and features of the present invention, wherein the brace includes a single leg strap and two foot straps instead of two leg straps and two foot straps.

FIG. 34 is a perspective view of another preferred rear-entry ankle brace 600 in accordance with one or more aspects and features of the present invention, wherein the brace 600 includes a single leg strap 602 and two foot straps 604, 606.

Figure 35:
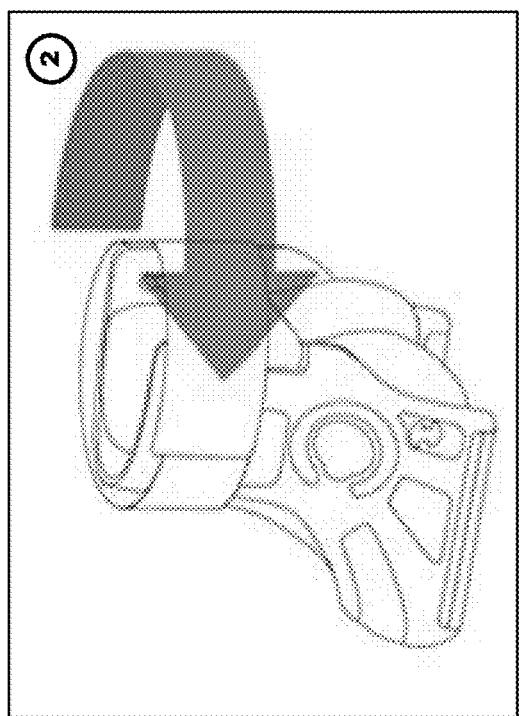
FIGS. 35 through 38 each illustrates a tag that preferably is sewn onto a strap for purposes of indicating to a wearer the sequence for securing the brace, all in accordance with one or more aspects and features of the present invention.
Figure 36:
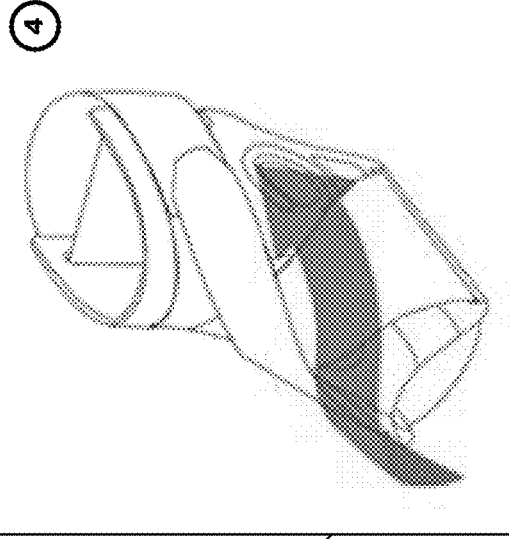
Figure 37:
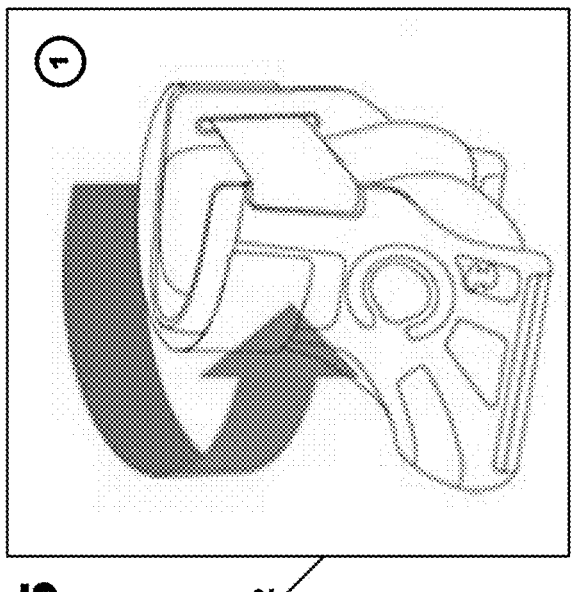
Figure 38:
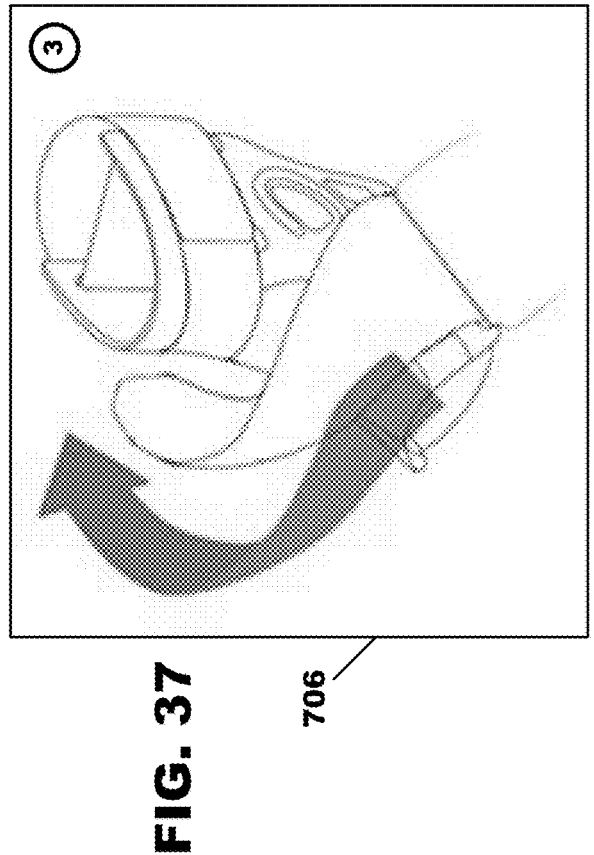

FIG. 35 through FIG. 38 each illustrates a tag that preferably is sewn onto a strap for purposes of indicating to a wearer the sequence for securing the brace, all in accordance with one or more aspects and features of the present invention. Specifically, FIG. 35 illustrates a first tag 702 showing the wrapping of a first leg strap around the leg portion of the brace and FIG. 36 illustrates a second tag 704 showing the wrapping of a second leg strap around the leg portion in the opposite direction and the attachment of the second leg strap to the first leg strap using, preferably, hook-and-loop fasteners. FIG. 37 illustrates a third tag 706 showing the subsequent wrapping of a first foot strap from a bottom edge of the foot portion diagonally upward and attachment of the end of the first foot strap to the first leg strap, preferably using hook-and-loop fasteners. Lastly, FIG. 38 illustrates a fourth tag 708 showing the subsequent wrapping of a second foot strap from an opposite bottom edge of the foot portion diagonally upward, across the first foot strap, and attachment of the end of the second foot strap to the first and/or second leg straps, preferably using hook-and-loop fasteners. The first tag 702 preferably is sewn or otherwise attached to an inside surface of the first leg strap; the second tag 704 preferably is sewn or otherwise attached to an inside surface of the second leg strap; the third tag 706 preferably is sewn or otherwise attached to an inside surface of the first foot strap; and the fourth tag 708 preferably is sewn or otherwise attached to an inside surface of the second foot strap. None of the tags preferably are visible when the brace is fully secured with the straps. For braces with a single leg strap, tag 704 preferably is omitted with tag 702 alternatively showing how to wrap the single leg strap back over itself and around the leg portion.

Returning now to FIGS. 7-21, preferred embodiments will be described in greater detail for a fuller understanding of aspects and features of the invention. With specific reference to rear-entry brace 10, this preferred brace 10 comprises an assembly of components including an elastomeric component 20, two leg straps 50, and two foot straps 80. The leg straps 50 are configured to encircle and secure the brace 10 to the leg, and the two foot straps 80 are configured to encircle and secure and secure the brace 10 to the foot.

The elastomeric component 20 itself comprises lateral and medial support systems 22 each made of an interlinking set of bands 23 which include supports or strut members 23 which radiate outwardly from a central ringed hub 25 that surrounds a respective malleolus on a side of the ankle. The lateral and medial support systems 22 are part of a joined transverse double arch, like an open elbow conduit or inside elbow channel, with one arch 26 for the lower leg and the transverse arch 28 for the mid-foot area. The support systems 22 include interstitial areas 30 that are more flexible. These areas or "fenestrations" can be open areas, or more preferably include an interconnecting or spanning web of softer material. The support systems 22 are joined in the front of the leg, and top of the foot in a front fold 32 formed by a fenestration in the general shape of a diamond. The combination of the double hubs 25 and support systems 22 and the front fold 32 form a self-hinge to permit the brace and ankle to hinge at an axis formed between the malleoli rings or hubs 25. Additionally, the hubs include a break or area of lower volume of material to encourage hinging about an ankle transverse to the medial plane of the brace and through the opposing hub members. The medial and lateral hub and strut systems 22 thereby are believed to inhibit torsion or twisting of the ankle (i.e., inversion or eversion).

The configuration of the elastomeric component 20 itself preferably has a mirror symmetry about the medial plane whereby the elastomeric component can be used for either a left or right ankle. The symmetry does not need to extend to the straps where it is possible that only one side of the brace includes a leg or foot closure strap, for example, which can double back on itself, or includes a D-ring attachment with a slotted opening to allow a mating strap to be feed through the slot.

So as to be a "rear-entry" brace 10, the elastomeric component 20 is open to the rear of the ankle and bottom of the foot (includes a longitudinal channel opening) whereby the brace 10 can be directly placed directly onto the foot from the front of the foot and closed at the top and around the mid-foot by two sets of closure means, such as adjustable straps, i.e., one leg strap or a set of two leg straps 50 at the top of the leg portion 26, and two foot straps 80 at the bottom of the foot portion 28.

Advantageously, the foot closure means 51 of the ankle brace 10 includes a pair of foot straps 80 that are connected to or extend from the bottom edge of the foot portion 28 of the elastomeric component. These straps 50 wrap under the foot and form a self-sole 52 and a plantar surface of the brace 10. The straps 50 can include provisions for additional support, or cushioning under the foot, or for additional rigidity, stiffness, or padding, as desired. Ideally, one strap 50 is attached to the elastomeric component 20 to allow the other strap 50 to feed through the elastomeric component, the strap, or the connection between the strap and the elastomeric component so that the foot straps 50 overlap to close the elastomeric component about the wearer's foot.

The foot straps 80 may comprise an elastomer or a stretch fabric, and in particular, the straps may have elastic portions that cross and wrap over the front of the ankle which add additional elastic variable resistance that is distributed through the elastomeric component to the ankle during use. This tensioned resistance can be tailored to individual use by slight changes in the direction and amount of pull in putting the brace on and by changing the angle or the location at which the strap ends are fastened on the leg straps that have mating fastening means.

The foot portion 28 has a distal opening 16 that may include a band member and that is configured to snugly surround the user's foot, at approximately the neck of the fifth metatarsal through the plantar surface to the middle of the first metatarsal and arching proximally toward the tibial fibular talar joint over the dorsal surface of the foot. At the other end, the foot portion 28 ends on the plantar side posterior to the end of the medial arch in a heel opening 18 which is behind the fat pad of the heel (approximately ½ of the way posterior toward the heel end of the calcaneus) on the posterior side, and below the insertion of the gastrocnemius into the Achilles tendon as it extends upward on the leg to form the bottom boundary of the leg portion of the brace. The foot portion 28 ends on the anterior side of the ankle at the "eye of the ankle", i.e., on the superficial aspect of the anterior ankle at the joint of the tibia/fibula/talus (or the "TFT" joint). The foot portion 28 includes a blanket or web of material (preferably molded or cast) that covers an area corresponding to the cuneiforms and the cuboid bone and the navicular bone. On the medial and lateral sides of the brace, the foot portion runs diagonally between the anterior and posterior openings where it joins the leg portion 26 which surrounds the bottom portion of the leg or the vertical portion of the ankle approximately ⅓ of the way up the lower leg, and below the bellies of the distal aspect of the gastrocnemius.

The leg portion 26 of the brace includes a pair of leg straps 80 that extend from the rear edges 38 of the leg portion 26 of the elastomeric component. Preferably, the closure means 81 of the leg portion includes two straps where one is connected to the leg portion of the elastomeric component such that the second leg strap can be threaded through a recess in the first strap, or in the elastomeric component, or in the connection between the strap and the elastomeric component, such as by the provision of a D-ring for re-enforcement of the connection to the elastomeric component 20 and to provide a slot which receives the opposing strap 80. The leg straps 80 wrap around the leg portion of the brace which may advantageously include a lip to help to hold the strap in position on the brace The leg straps further include fastening means, such as a segment of a hook and loop landing pad that serves to receive the fastener opposing segment on the other leg strap 80, and further which anchors the ends of the foot straps 50 which extend upward from the bottom of the foot portion 28 of the elastomeric component 20 and form an foot strap portion that is thinner in width where they cross diagonally over each other in a figure of eight design (best represented in FIG. 1) and have a closure means such as a terminal tab with hook or loop on the interior side and which fastens on the landing pad of the leg strap 80. This provides a figure of eight over the front of the ankle joint to stabilize the syndesmosis. This portion of the foot straps can have an elasticity that is engineered for greater or less stretch to provide the desired flex and support at this vulnerable part of the ankle.

Thus, the invention generally provides an athletic and/or therapeutic orthopedic brace or support 10 which comprises an elastomeric component 20 having integrally formed interlinking bands that resist and direct active forces joined together for greater stability by thinner and more flexible or elastic webs of material in the interstitial spaces, which are referred to herein as "fenestrations". The term "fenestrations" are used herein to refer to areas of reduced support, which may be openings or which may include a webbed area of a softer or more yielding material characterized by a lower durometer material, preferably having perforations to allow the webbed area or webs of material to allow perspiration to pass through. Advantageously, the web of material is formed as thinner areas of the same material as the support bands, so that the elastomeric component can be formed as an integral unit, such as by molding the elastomer.

Preferably the elastomeric component 20 includes two sets of interconnected opposing support systems 22 which have a central ring or hub 25 joined to radiating strut or support members 23. The interconnected opposing support systems are designed to encourage the brace to allow pivoting motion at the ankle joint, but to inhibit twisting or movement off-axis. This allows the ankle to continue to function as a hinge for athletics while helping to protect a vulnerable ankle. Thus, the brace surrounds and supports the ankle so as to provide an external anatomically configured framework that mimics or augments the effects of the ligaments, and further acts to rebound or re-direct dynamic forces that the ankle generates or encounters. In the environment of the brace, the invention includes a self-formed hinge system that is engineered to allow motion in a controlled manner, so that the supported joint may be flexed in a direction that is not harmful but where potentially harmful motion is inhibited by the brace.

The integral elastomeric component member 20 includes a pair of central support structures 22 (i.e., the lateral and medial malleoli support members or rings) that together define an axis of motion across the malleoli. The support member preferably comprises opposing hub members, such as on the medial and lateral side of the ankle, (or possibly in further embodiments for the knee or elbow joint) which members together define an axis about which a first member of the brace hinges or pivots relative to a second member of the brace. Together these hub members include an opening or weakened area in the middle which overlays the ankle bones (i.e., malleoli) to define an axis about which the ankle hinges and which the brace permits while still inhibiting movement in other planes, such as torsion or twisting. The two sets of support members are joined to from two to eight strut members 23 or bands which radiate away from the support members to form a vertical side support on each side. Advantageously, the elastomeric component 20 demonstrates mirror symmetry from the lateral and medial side so that the elastomeric component 20 can be worn on either a left or right ankle (i.e., is "universal"). The medial and lateral support systems comprised of the central hub and radiating struts are joined together over the top of the foot and front of the ankle in a fenestration that is preferably diamond shaped, again to permit flexing about the ankle joint during permitted movement.

The brace further includes negative or void areas, such as weakened areas, recesses or apertures that act to re-direct forces through the complementary areas which assume the stresses in response to the existence of the negative area. The weakened areas can comprise complimentary webs of softer, more yielding, lower durometer material, e.g., having a durometer of 35+/−10, and preferably 45+/−5 5, on the Shore A scale. This material may also include perforations, such as pores or holes of 0.0001-0.05 inch diameter, to allow for the evaporation of perspiration. These pores may also affect the softness of the material.

The higher stiffness (or lower elasticity or resistance to stretch) can be effected by a number of methods, including a change in material, a change in material characteristics, including cross-linking or durometer which can be caused by the manufacturing method or by the ingredients, or a change in the geometry, including thicker or wider or higher volume of material so as to direct, inhibit or manipulate forces transmitted to the affected joint during use.

Embodiments of the invention thus relate to generally to a soft, flexible, elastomeric universal rear-entry ankle brace for use under a shoe and which is engineered to deform so as to allow and direct a preferential direction of movement through the support system. The brace is a universal brace, meaning that a single brace is designed for use on either the left or right ankle of a wearer. It is further designed to allow for a wide range of adjustment in the circumferential shape of the foot and ankle to minimize inventory and sizing requirements. This is achieved by providing a molded elastomeric elbow-shaped elastomeric component with a front leg portion and a front foot portion which has a structure with mirror symmetry about a medial plane. The elastomeric component has a thickened interlinking framework with central rings and radiating struts interconnected with areas of less thick perforated webs of material. The back of the elastomeric component is open to allow the wearer to put the brace on and a set of top (proximal) straps encircles the leg at the top of the brace to close the brace about the leg.

Advantageously, the support system members comprise a network of elastomeric supports, (preferably band members that are longer than they are wide and wider than they are thick so as to comfortably distribute the tension that they apply to the user) and also includes a plurality of strut members (once again elastomeric band members) comprising a first set of struts on the medial side of the ankle brace and a second set of struts on the lateral side of the ankle. The medial set of struts radiate outwardly from the medial support or hub and are linked to the periphery of the brace on the medial side and the lateral set of struts radial outwardly from the lateral support or hub and are linked to the periphery of the brace on the lateral side of the brace. The bottom of the elastomeric component is open and a set of overlapping foot straps form a planar surface and close the foot portion of the brace. The ends of the foot straps cross each other across a front fold of the brace over the front of the ankle joint and the foot straps fasten by means of hook and loop on the exterior leg strap. On one side a leg strap is joined to the elastomeric component with a slot opening for the other leg strap which allows the straps to overlap each other, and a similar structure joins the foot straps to allow over-lapping. The slot is advantageously formed using a D-ring reinforcement connector.

The straps can include means for fastening or adjustment, including for example, the hook-and-loop fasteners such as those of a Velcro™ fastening assembly. The mating portion of the fastening means can advantageously be held on straps that extend from the rear of the brace, such as a medial strap and a lateral strap which encircle the ankle or which spiral about the ankle so as to direct the tension of the brace around the ankle, and around the brace.

The spaced support systems act to limit the lateral motion (i.e., side to side or torque or twisting) while allowing the hinging of the brace much in the way that the spokes of a wire spoked wheel or the cables of a tension bridge act to support the elastomeric component in tension while the elastomeric component accepts and transmits compressive forces. In accordance with this invention, the support systems 22 are engineered to allow for preferential deformation of the shape of the support, for example, by hinging at the front fold provided by the diamond fenestration 32 at the front of the ankle, to preferentially allow or direct motion within or at the support member or members. More specifically, the support member at each the malleolus includes a section of reduced rigidity, such as a section of reduced volume (including a reduced width, thickness, or absent length i.e., a discontinuity such as a notch or gap) so as to encourage the deformation of the support at a specific location or for example, for a ringed band, a defined buckling or lapping which allows the first and second brace parts to hinge about an axis defined by the support member or hub 25. Alternatively, the section can be a section of material having increased elasticity, such as an area in which there is a lesser degree of cross-linking. The malleoli supports are generally ringed support members (i.e., bands) that from a complete 360° circuit (optionally in some embodiments of the hinge member minus a small section such as 1-20°, and preferably 2-10°, and most preferably 3-7°), which may advantageously be a circle, oval, or ellipse, but which also form a linear support, such as a quadrangle, or a hexagon or geometric shape. Thus, the brace encourages motion, including rebound or re-coil in the permitted direction while inhibiting motion that is more likely to have the potential to harm the joint.

In the exemplary ankle brace, the set of struts 23 (i.e., elastomeric bands which act in tension as struts) thus includes one or two upwardly extending strut members that join at the bottom to the malleolus support or hub and on the top to a proximal portion of the brace network and one or two diagonally extending strut members that extend from the medial support or hub to a distal portion of the brace network (the proximal and distal portions can optionally include bands to further re-enforce and distribute tension, although the foot and leg straps can serve this function so as to eliminate the need for the end bands and allow for easier accommodation of a shoe). Each bottom edge of the elastomeric component is joined to a foot strap that lays against the plantar surface of the foot and extends upward and diagonally over the front of the ankle to cross over the front fold. These straps can include areas of differing stretch so as to engineer the amount of give and support that the straps provide for the syndesmosis. The back edges 38 of the elastomeric component includes a set of leg straps 80 that wrap around the top of the elastomeric component 20 to close the brace about the leg. At least one of the straps includes an exterior section of hook or loop as a landing area for fastening the foot straps and the mating leg strap. This configuration of the brace allows a rear entry brace which closes around the front in such a way that the closure means serve primarily for sizing and tightening, and are not subject to the direct forces that tend to cause closure means to wear out, for example, when the hook and loop of Velcro™ is tensioned along the direction of fastening.

The hinge system of the invention can be used in braces which are used prophylactically (for example, allowing sufficient range of motion to allow the brace to be worn during athletic activities without hindering the athlete, but which acts to support the joint or joint complex and to inhibit potentially harmful motion) or the brace can be used therapeutically (for example, in the aid of healing of a joint or joint complex which has suffered some previous injury). The brace has application in all of the joints, including the shoulder, elbow, wrist, hand, thumb, foot, knee, hip and back and the concepts of the present invention can be applied to each of these joint complexes, but is illustrated specifically with respect to an ankle brace.

Thus, the brace of the current invention is designed to allow as much safe freedom of movement to the wearer as possible, but to provide resistance to movement that could be harmful. In particular, the device is intended to inhibit inversion in plantar flexion (and to help stabilize the syndesmotic ligament) so as to avoid "rolling" an ankle. The brace is intended to provide external support tantamount to external ligaments and or fascia, which reinforces in proper places but which relieves pressure where it is needed. Thus, the device acts in tension and compression to buttress the syndesmotic ligament at the top, and in the cross-configuration to buttress the ATFL (anterior tibiofibular ligament), and the CFL (calcaneal fibular ligament), with a medial web member that buttresses the deltoid ligament. In addition, the elastomeric nature of the brace material, and in particular of the hinge system, coupled with the form can act to provide energy re-balance to the wearer, where the kinetic energy is re-circulated or re-coiled to the user, while inhibiting potentially dangerous forces applied to the joint complex. The material also provides proprioceptive feed-back to the user and the elasticity and/or stickiness of the material helps to remind the user to maintain tone. It is preferable that the material is "alive" or slightly sticky to the skin of the wearer. A desirable level of stickiness would be the feel of slightly under-cured natural latex, or a material that has been exposed and allowed to dry to a solution of sugar-water, or something less adhesive than a traditional band-aid or a light masking tape. Acceptable values measured according to ASTM, D3330D/D3330M, Test Method F at 90°, for peel adhesion of pressure sensitive tape, would be 0.0005-50 N/100 mm, preferable 0.5-30 N/100 mm, and most preferably 0.2-25 N/100 mm.

In a further embodiment of the invention, a pair of additional, and optionally internal adjustable vertical supports 150 or "stirrups" are provided to provide joint stability against typical directions of ligament strain. Specifically, as relates to the brace of the present invention in use for ankle support, the stirrups are provided as one or more additional add-on more rigid (as compared to the elastomeric component) elastomeric members that extend vertically up the lateral and/or medial aspect of the brace at the malleoli, and optionally including an opening over the malleoli to provide one or more line of support about the ankle joint. The pair of stirrups have mirror outlines with a rounded bottom portion 152 having a central opening 154 for a malleolus and upwardly extending front 156 and back 158 portions having a medial slot opening 160 with a horizontal connection 162 or bridge which joins the two front 156 and back 158 sections to stabilize them. The interior of the stirrup is formed in a generally cylindrical shape with a more convex section leading to the central opening such that a generalized mating shape to the lateral or medial topography of the ankle is formed. The stirrups are used on both sides of the ankle to give vertical stability and initially can be used with tape, and then mounted on the interior of the brace for a more active rehabilitation. They have easy attachment means 170 that cooperate with the brace 10, such as a button 172 which engages an opening 174 in the elastomeric component 20.

In addition, the elastomeric nature of the brace material, coupled with the form can act dynamically to provide energy re-balance to the wearer, where the kinetic energy created in a muscular exertion of the user is re-circulated or re-coiled to the user, while inhibiting potentially dangerous forces applied to the joint complex. The "spring" that results, and the resilient contact of the brace with the surface of the ankle, also provides a proprioceptive feel to the user that helps to protect the ankle joint. Thus, the brace can be used to train the exertion or exercise the foot and ankle of the wearer.

It is of advantage that the support means act to inhibit stress to the syndesmotic ligament, to the TFTL, and to the TCL. Thus, the foot straps provide support means which advantageously extend from the plantar support diagonally upward across the anterior hinge of the ankle in the vicinity of the cuboid and navicular bones, and possibly even to a further support member or anchor at the proximal end of the lower leg portion of the brace. These means can include straps that are designed so as to provide for adjustable degrees of tensioning, as well as adjustable directions of tensioning to allow the wearer to customize the feel and size. The device acts in tension and compression to buttress the syndesmotic ligament at the top, and in the cross-configuration to buttress the ATFL (anterior tibiofibular ligament), and the CFL (calcaneal fibular ligament), with a medial web member that buttresses the deltoid ligament.

The present invention is designed to provide some syndesmosis stability above the malleoli. In a further adjustable embodiment, it illustrated with a rear entry, i.e., open toward the posterior portion of the leg, but with an adjustable closure fixation point more anterior or anterolateral, (preferably not medial), with tension from posteromedial to lateral so as to pull the fibula anteriorly to help with syndesmosis stability and ankle. The superior leg band is comprised of a reasonably high tensile strength to protect the syndesmosis. The brace is designed to provide a definite end to plantar flexion and inversion and also some level of protection on the syndesmosis.

These support systems should have a definite endpoint at say 90-110% of physiological plantar flexion/inversion before easing to a firm stop at which point there is recoil. The struts are band members which are from 2-10× (and preferably from 3-8×, and most preferably from 4-6×) as wide as they are thick. The elastomeric component member of the brace is intended to be very tight on the user with a low tensile strength and durometer so that it molds well to the ankle. The struts have a high tensile strength that eases to a firm end-point before recoiling. In addition, tensioning or closure mechanisms permit the wearer to pull through them and get a feel of tension, which provides a reassuring feel to the wearer. This tension is set such that it could result in a very high tensile strength at the end of range of range so that it can be really quite stiff within a range that is totally safe for the user. Optional closure mechanisms include various mechanisms, such as hook-and-loop fasteners, e.g., Velcro™ fasteners.

Advantageously, the foot and leg straps each provides for ½ to 1 centimeters of adjustability, (in particular if the brace is provided in three sizes), depending on the material of the tensioning means and the size range for which the brace is intended.

In addition, in a further embodiment, the brace is illustrated as including a framework of a stiffer, i.e., higher durometer material, of approximately 60 durometer +/−15, preferably +/−10 and most preferably +/−5 on the Shore A scale. Advantageously, the foot portion 28 also includes at least two, but optionally more, (i.e., two three, four or more), symmetrically placed about the medial plane, v-shaped (or other shape which include a wider opening and a tapering portion which resists but will allow for expansion of the circumference of the ring) gussets which allows the proximal opening to expand without losing its function as an anchor in order to allow for size variations of the wearer. The fenestrations in this case, are actually areas of integrated softer material, for example having a durometer of 40+1/−10, and preferably +/−5 on the Shore A scale. This material is a relatively soft sheet of elastomeric material, with a uniform thickness from surface to surface, which is slightly sticky to the touch, as can be formed by injection molding or by casting at a lower cross-linking. This softer portion can also include perforations to allow for perspiration, or can include texturing to the surface for proprioceptive reasons. The web portion at the gusset may be advantageously strengthened, for example by eliminating the perforations in the remainder of the web in order to provide for greater strength here since the front of the network is open from the network to provide for greater fit.

The brace 10 is made, for example by molding such as injection or transfer molding, liquid silicone molding or reaction in mold casting, a bio-compatible elastomer from a material of suitable durometer to provide the desired fit, and elastomeric characteristics. The brace preferably is made of a material that exhibits equal stretch in at least two dimensions (i.e., the X, Y directions). This material can be made more resistant to provide further support, for example of the syndesmotic ligament, by various means, including the additional of supports or struts which might be provided by an integral (same material) thickening of the brace in a defined area, or by changes in the material itself, such as higher rate of cure or cross-linking or the addition of other materials such as reinforcing fibers or the use of a second elastomeric material having greater resistance to an applied force, like a higher durometer or Young's modulus or modulus of elasticity, and which could be embedded in the brace, co-molded, or adhered to the inside or outside of the brace. The brace is designed to allow motion with a limited end-point; to encourage the recoil of energy and to allow for the potential prevention of harmful forces, i.e., the brace permits motion that is safe within a defined range, but inhibits abnormal or dangerous motion.

The brace 10 is intended to be very tight on the user with a low tensile strength and durometer so that it molds well to the ankle. The material of the brace is ideally an elastomer, including for example, a thermoplastic elastomer having a Shore A hardness of 2-75 at 10 sec when measured in accordance with ASTM D2240, and a tensile break at stretch of 2-6 MPa at 23° C. using Die C2 hour when measured in accordance with ASTM D412, tensile stress of 0.08 to 0.8 MPa at strain 100% and 0.2 to 1.5 MPa at 300% at 23° C. using Die C2 hour when measured in accordance with ASTM D412, and an Elongation at break of 800-1200% at 23° C. using Die C2 hour when measured in accordance with ASTM D414, a tear strength of 7.5-20 kN/m when measured in accordance with ASTM D624, and a compression set of 5-30% at 23° C. and at Time 79200 sec when measured in accordance with ASTM D395. Thermoplastic elastomers are suitable materials, alone, or compounded with additional materials, such as other cross-linking agents, additional elastomers to achieve material characteristics, reinforcing fibers and fillers, antimicrobial agents, colorants, and fragrances. The brace 10 could further include a fabric backing over an entire surface or over portions of a surface in order to control the directions of resistance including a weave such as a bias weave fabric, which limits the stretch to one axis and inhibits the stretch along the other two axes.

The through thickness of the elastomeric component will depend on the material and elasticity but is preferably "low profile" meaning that it can be worn, optionally with socks, under a user's shoe, meaning that it does not require a different size than is worn without the brace. Preferably the thickness would be form 2-to-10 mm, and more narrowly 5-8 mm.

It further will be appreciated from the foregoing that embodiments of the invention provide a dynamic brace assembly having an elastomeric component with a pair of associated foot straps and at least one leg strap, and preferably a pair of leg straps, which fastens the elastomeric component about the leg and foot. The brace assembly is "universal" insofar as the brace assembly can be worn in support of the left ankle or the right ankle. Furthermore, the elastomeric component comprises an opposing set of lateral and medial support systems made of an interlinking set of bands or strut members which radiate outward from a central ringed hub that surrounds the malleoli. This design is "dynamic" insofar as it allows for the directional transfer of dynamic forces through the band system and as further stabilized and mediated through the intermediate spaces of thinner, perforated webbing, which also allows for air and perspiration to pass through the brace. In addition, the band system and intermediate webbing may be integrated or formed from one homogenous material, such as by molding or casting with the bands being thicker so as to be less elastic than the webbing.

The opposing set of lateral and medial support systems are part of a unitary joined transverse double arch, like an open elbow conduit or "inside elbow channel", with one arch for the lower leg and the transverse arch for the mid-foot area. Here, transverse is used loosely, where the angle between the medial axes of the lower leg and the foot arches may be 90°+/−25°, and preferably +/−15°, or 10°. The support systems are joined in the front of the leg, and top of the foot in a front fold formed by a fenestration in the shape of a diamond with the side angles corresponding to the hubs at the malleoli. The combination of the double hub and strut support systems and the front fold form a self-hinge to permit the brace and ankle to hinge at an axis formed between the malleoli rings or hubs. The malleoli rings have an interrupted or thinned area to encourage the hinging action of the brace and permit comfortable wear during active use.

The medial and lateral hub and strut systems inhibit torsion or twisting of the ankle (i.e., inversion or eversion). The functional configuration (i.e., the outline, through shape and topography) of the elastomeric component has mirror symmetry about the medial plane of the elastomeric component in order that the elastomeric component can be used for either a left or right ankle. The symmetry does not need to extend to the connection for the straps, as it is possible for example that only one side includes a D-ring attachment with a slotted opening to allow a mating strap to be feed through the slot.

The elastomeric component is open to the rear of the ankle and bottom of the foot to allow the brace assembly to be rear entry, meaning that it can be placed or slid onto the foot from the top or front of the foot and closed by two sets of adjustable straps, one strap or set of straps at the top of the leg portion, and one set of at least two straps at the bottom of the foot portion.

The ankle brace includes a pair of foot straps that are connected to or extend from the bottom edge of the foot portion of the elastomeric component. These straps wrap under the foot and form a self-soul for the plantar surface. In further embodiments, the brace can include a soul, or be directly incorporated into a shoe. The straps can include provisions for additional support, or cushioning under the foot, or for additional rigidity, stiffness, or padding Ideally, one strap is attached to the elastomeric component to allow the other strap to feed through the elastomeric component, the strap, or the connection between the strap and the elastomeric component so that the foot straps overlap to close the elastomeric component about the foot. The straps may include areas of varying stretch, such as an area where one is joined to the elastomeric component which does not stretch and an adjacent area that does stretch, or a terminal area with hook and loop fastening means that does not stretch.

Likewise, the leg portion of the brace includes at least one leg strap that extends from the rear edge of the leg portion of the elastomeric component. Preferably, the leg portion includes two straps, again, where one is connected to the leg portion of the elastomeric component such that the second leg strap can be threaded through the strap, the elastomeric component, or the connection between the strap and the elastomeric component, such as by the provision of a d-ring for re-enforcement of the connection and to provide a slot which receives the opposing strap. The leg straps wrap around the ankle to seat below a lip at the top of the leg portion of the brace. One or both of the leg straps includes a segment of a hook and loop landing pad that serves to receive the opposing segment on the other leg strap, and further which anchors the ends of the foot straps which extend upward from the bottom of the foot portion of the elastomeric component and thin in width where they cross diagonally over each other and fasten to the leg strap. This provides a "figure of eight" over the front of the ankle joint to stabilize the syndesmosis.

Embodiments of the invention further relate to a pair of vertical stabilizers or stirrup members that can be used in conjunction with the brace or independently thereof. The stirrup members have complex topographies which are roughly portions of cylinders to fit around an ankle from 1 to 3 inches below the malleolus to 3 to 6 above the malleolus on each side with co-extensive inner and outer surfaces more specifically shaped to cradle the lateral and medial sides of the ankle joint and provide vertical support. The stirrups are generalized to a universal pair for left and right usage without specific right and left lateral and medial members with a roughly rectangular outline of sufficient height to extend above an ankle bone by several inches (i.e., 5.5+/−2 inches). The stirrups each have a central opening that has a longer upright portion which extends into a rounded or diagonal oval bottom to surround and support the malleolus. The central slot opening extends from the top edge of the stirrup to a round opening near the bottom for a malleolus. Partway near the top (i.e., about 1-3 inches down or from ⅕ to ⅓ of the height of the opening), the slot includes a small linking member or bridge that connects the front and back portions of the stirrup. The stirrup further includes at least one, and preferably two or more button fasteners that can feed through a corresponding opening in the brace member. These are advantageously located near the linking member but behind or in front of the slot, and centrally below the malleolus opening in the central slot opening.

Preferred ankle braces of the invention are soft and flexible. It is thin and comfortable for daily wear under a shoe, as part of a daily routine and during athletics. It permits safe movement and guards against twisting or torsion that could harm vulnerable soft tissue. The elastomeric properties of the material from which it is made, along with the form provided by bands of thicker areas of material and interstitial fenestrations of thinner areas of material, cause the brace to be dynamic, i.e., to direct energetic forces through the brace during use to rebound the forces that the user applies and encounters during wear, including to create proprioception and to exercise the many fine co-ordinations of the foot and ankle system. The design is a universal design which greatly simplifies the complexities of manufacturing and inventory since the brace can be worn on the left or right ankle and provides for adjustment such that a wide range of individual ankle size and confirmation can be accommodated by a very few set of sizes, such as a small, medium, and large size brace. A pair of semi-rigid stirrups are provided for use under the brace for more therapeutic applications and in the early phases for rehabilitation from injury. A set provides opposing stirrups which can be interchanged as the medial and lateral stirrups so a single set work for both the left and right ankle and also to accommodate a variety of ankle shapes and sizes. Each stirrup is designed to provide vertical stability with a circumferential flexibility.

Based on the foregoing description, it will be readily understood by those persons skilled in the art that the invention has broad utility and application. Many embodiments and adaptations of the invention other than those specifically described herein, as well as many variations, modifications, and equivalent arrangements, will be apparent from or reasonably suggested by the invention and the foregoing descriptions thereof, without departing from the substance or scope of the invention. Accordingly, while the invention has been described herein in detail in relation to one or more preferred embodiments, it is to be understood that this disclosure is only illustrative and exemplary of the invention and is made merely for the purpose of providing a full and enabling disclosure of the invention. The foregoing disclosure is not intended to be construed to limit the invention or otherwise exclude any such other embodiments, adaptations, variations, modifications or equivalent arrangements, the invention being limited only by the claims appended hereto and the equivalents thereof.

What is claimed is:

1. A method of donning a rear-entry ankle brace, the brace comprising,
 an elastomeric component having a distal end portion comprising an arched foot portion, a proximal end portion comprising an arched leg portion, and an intermediate portion extending between the foot portion and the leg portion and comprising an arched ankle portion, wherein a channel opening extends along a length of the elastomeric component from the distal end portion to the proximal end portion,
 first and second leg straps secured to and extending from first and second rear edges of the channel opening in an area of the leg portion, and
 first and second foot straps secured to and extending from first and second bottom edges of the channel opening in an area of the foot portion,
 the method comprising the steps of:
 (a) positioning the elastomeric component directly onto a mid-foot, lower leg portion, and ankle joint of a wearer without passing the mid-foot through the proximal end portion such that the elastomeric component spans the ankle joint of the wearer with the distal end portion extending over and covering a top and sides of the mid-foot of the wearer, with the proximal end portion extending over and covering a front and sides of the lower leg portion of the wearer, and with the intermediate portion extending over and covering a front and sides of the ankle joint of the wearer;

(b) tensioning the first and second rear edges toward one another and securing the leg portion to the lower leg of the wearer by tensioning and securing the first and second leg straps; and (c) tensioning the first and second bottom edges toward one another and securing the foot portion to the mid-foot of the wearer by tensioning and removably attaching each of the first and second foot straps to one of the first and second leg straps, with the first and second foot straps spanning the channel opening in the area of the foot portion, with the first foot strap overlapping and extending under the second foot strap in spanning the channel opening in the area of the foot portion such that the first foot strap defines a plantar surface of the brace, and with the second foot strap extending through a slot located at one of the first and second bottom edges of the channel opening from where the first foot strap extends.

2. The method of claim 1, wherein the first and second leg straps span the channel opening between the first and second rear edges and overlap one another, and wherein the brace further comprises a slot located at one of the first and second rear edges of the channel opening in the area of the leg portion at a location from where one of the first and second leg straps extends, through which slot the other of the first and second leg straps extends.

3. The method of claim 2, wherein the slot through which the other of the first and second leg straps extends is defined by a D-ring that is at least partially embedded within the elastomeric component.

4. The method of claim 1, wherein the slot through which the second foot strap extends is defined by a D-ring that is at least partially embedded within the elastomeric component.

5. The method of claim 1, wherein the first and second foot straps extend diagonally upward from the first and second bottom edges of the channel opening and cross over each other along the intermediate portion of the elastomeric component when tensioned and attached in said step (c).

6. The method of claim 1, wherein each said foot strap is removably attached to the leg strap using hook and loop fasteners.

7. The method of claim 1, wherein the elastomeric component consists of a single molded piece of one or more thermoplastic materials.

8. The method of claim 1, wherein the elastomeric component further defines, on each of opposite lateral and medial sides of the brace, a central hub with radiating struts extending from the central hub and with interstitial areas extending between the radiating struts; and wherein the interstitial areas comprise areas that are substantially thinner than the radiating struts and that include perforations extending through the elastomeric component for breathability of the brace when worn.

9. The method of claim 1, further comprising donning a shoe while the brace is being worn, with the leg portion extending above the shoe and the foot portion being received within the shoe.

10. The method of claim 1, wherein said steps (b) and (c) are performed together.

11. A method of donning a rear-entry ankle brace, the brace comprising, an elastomeric component having a distal end portion comprising an arched foot portion, a proximal end portion comprising an arched leg portion, and an intermediate portion extending between the foot portion and leg portion and comprising an arched ankle portion, wherein a channel opening extends along a length of the elastomeric component from the distal end portion to the proximal end portion, a leg strap extending from first and second rear edges of the channel opening in an area of the leg portion, and first and second foot straps secured to and extending from first and second bottom edges of the channel opening in an area of the foot portion, the method comprising the steps of:

(a) positioning the elastomeric component directly onto a mid-foot, lower leg portion, and ankle joint of a wearer without passing the mid-foot through the proximal end portion such that the elastomeric component spans the ankle joint of the wearer with the distal end portion extending over and covering a top and sides of the mid-foot of the wearer, with the proximal end portion extending over and covering a front and sides of the lower leg portion of the wearer, and with the intermediate portion extending over and covering a front and sides of the ankle joint of the wearer;

(b) tensioning the first and second rear edges toward one another and securing the leg portion to the lower leg of the wearer by tensioning and securing the leg strap; and (c) tensioning the first and second bottom edges toward one another and securing the foot portion to the mid-foot of the wearer by tensioning and removably attaching each of the first and second foot straps to the leg strap, with the first and second foot straps spanning the channel opening in the area of the foot portion, with the first foot strap overlapping and extending under the second foot strap in spanning the channel opening in the area of the foot portion such that the first foot strap defines a plantar surface of the brace, and with the second foot strap extending through a slot located at the bottom edge of the channel opening from where the first foot strap extends.

12. The method of claim 11, wherein the leg strap twice spans the channel opening between the first and second rear edges and overlaps itself, and wherein the brace further comprises a slot along one of the first and second rear edges of the channel opening in the area of the leg portion through which the leg strap extends.

13. The method of claim 12, wherein the slot through which the leg strap extends is defined by a D-ring that is at least partially embedded within the elastomeric component.

14. The method of claim 11, wherein the slot through which the second foot strap extends is defined by a D-ring that is at least partially embedded within the elastomeric component.

15. The method of claim 11, wherein the first and second foot straps extend diagonally upward from the first and second bottom edges of the channel opening and cross over each other along the intermediate portion of the elastomeric component when tensioned and removably attached in said step (c).

16. The method of claim 11, wherein each said foot strap is removably attached to the leg strap using hook and loop fasteners.

17. The method of claim 11, wherein the elastomeric component consists of a single molded piece of one or more thermoplastic materials.

18. The method of claim 11, wherein the elastomeric component further defines, on each of opposite lateral and medial sides of the brace, a central hub with radiating struts extending from the central hub and with interstitial areas extending between the radiating struts; and wherein the interstitial areas comprise areas that are substantially thinner than the radiating struts and that include perforations extending through the elastomeric component for breathability of the brace when worn.

19. The method of claim 11, further comprising donning a shoe while the brace is being worn, with the leg portion extending above the shoe and the foot portion being received within the shoe.

20. The method of claim 11, wherein said steps (b) and (c) are performed together.

* * * * *